US012510541B2

(12) United States Patent
Hellal et al.

(10) Patent No.: US 12,510,541 B2
(45) Date of Patent: Dec. 30, 2025

(54) METHODS FOR PURIFICATION, DETECTION AND QUANTIFICATION OF RESIDUAL PEI-BASED TRANSFECTION REAGENTS

(71) Applicant: POLYPLUS TRANSFECTION, Illkirch-Graffenstaden (FR)

(72) Inventors: Malik Hellal, Illkirch (FR); Patrick Erbacher, Benfeld (FR); Yann Philipson, Brumath (FR); Sébastien Franck, Geispolsheim (FR); Elodie Wohlfrom, Fegersheim (FR)

(73) Assignee: POLYPLUS TRANSFECTION, Illkirch-Graffenstaden (FR)

( * ) Notice: Subject to any disclaimer, the term of this patent is extended or adjusted under 35 U.S.C. 154(b) by 0 days.

(21) Appl. No.: 18/730,678

(22) PCT Filed: Feb. 24, 2023

(86) PCT No.: PCT/EP2023/054664
§ 371 (c)(1),
(2) Date: Jul. 19, 2024

(87) PCT Pub. No.: WO2023/161409
PCT Pub. Date: Aug. 31, 2023

(65) Prior Publication Data

US 2025/0116667 A1 Apr. 10, 2025

(30) Foreign Application Priority Data

Feb. 25, 2022 (EP) .................................... 22305218

(51) Int. Cl.
*C08G 73/02* (2006.01)
*A61K 47/59* (2017.01)
*C12N 15/86* (2006.01)
*C12Q 1/70* (2006.01)
*G01N 33/53* (2006.01)
*G01N 33/569* (2006.01)

(52) U.S. Cl.
CPC ... *G01N 33/56983* (2013.01); *C08G 73/0233* (2013.01); *C12N 15/86* (2013.01); *C12Q 1/70* (2013.01); *G01N 33/5308* (2013.01); *G01N 2333/015* (2013.01)

(58) Field of Classification Search
CPC ...... C08G 73/0233; C12N 15/86; C12Q 1/70; G01N 33/5308
See application file for complete search history.

(56) References Cited

U.S. PATENT DOCUMENTS

| | | | |
|---|---|---|---|
| 2010/0197888 | A1 | 8/2010 | Adib et al. |
| 2011/0091407 | A1 | 4/2011 | Cheradame |
| 2018/0094017 | A1 | 4/2018 | Kitade et al. |

FOREIGN PATENT DOCUMENTS

| | | | |
|---|---|---|---|
| CN | 101821317 | A | 9/2010 |
| CN | 102260376 | A | 11/2011 |
| CN | 111032869 | A | 4/2020 |
| WO | 2016152980 | A1 | 9/2016 |
| WO | 2019014924 | A1 | 1/2019 |
| WO | 2021023796 | A1 | 2/2021 |
| WO | 2021023798 | A1 | 2/2021 |

OTHER PUBLICATIONS

Laycock, Bronwyn, et al. "Lifetime prediction of biodegradable polymers." Progress in Polymer Science 71 (2017): 144-189. (Year: 2017).*

Jeong, Ji Hoon, et al. "DNA transfection using linear poly (ethylenimine) prepared by controlled acid hydrolysis of poly (2-ethyl-2-oxazoline)." Journal of controlled Release 73.2-3 (2001): 391-399. (Year: 2001).*

Fernandes, Julio C., et al. "Linear polyethylenimine produced by partial acid hydrolysis of poly (2-ethyl-2-oxazoline) for DNA and siRNA delivery in vitro." International journal of nanomedicine (2013): 4091-4102. (Year: 2013).*

Borst, Annemarie, A. T. A. Box, and A. C. Fluit. "False-positive results and contamination in nucleic acid amplification assays: suggestions for a prevent and destroy strategy." European journal of clinical microbiology and infectious diseases 23 (2004): 289-299. (Year: 2004).*

Zhang, Tao, et al. "Quantitative analysis and degradation mechanisms of different protein degradation methods." Journal of Biomedical Materials Research Part B: Applied Biomaterials 110.5 (2022): 1034-1043. (Year: 2022).*

International Search Report and Written Opinion of the ISA for PCT/EP2023/054664, mailed May 24, 2023, 13 pages.

EP Decision to Grant a European Patent for EP22305218.4, dated Jun. 20, 2024, 2 pages.

Merck webpage, author unknown, BioReliance Product Characterization Services, Assay Packages, Process and Product Impurities, Process Impurity Testing: Polyethylenimine (PEI), Sep. 20, 2019, XP055949741, 2 pages.

Office Action, issued in Japanese Patent Application No. 2024-548750 dated Mar. 18, 2025.

Office Action, issued in Chinese Patent Application No. 202380022661.1 dated Mar. 8, 2025.

* cited by examiner

*Primary Examiner* — Abigail Vanhorn
(74) *Attorney, Agent, or Firm* — NIXON & VANDERHYE

(57) ABSTRACT

The present invention relates to methods for purification, detection and quantification of residual PEI-based transfection reagents. The present invention is directed to a method for performing an acidic hydrolysis of a liquid mixture comprising a biological matrix and a polyethyleneimine (PEI)-based transfection reagent of general formula (I) as described herein, wherein the biological matrix comprises a recombinant virus or virus-like particles produced using the PEI-based transfection reagent, and wherein said acidic hydrolysis does not degrade the PEI-based transfection reagent. The present invention also relates to a method for purifying, detecting and/or quantifying a PEI-based transfection reagent of general formula (I) as described herein.

11 Claims, 3 Drawing Sheets

(I)

METHODS FOR PURIFICATION, DETECTION AND QUANTIFICATION OF RESIDUAL PEI-BASED TRANSFECTION REAGENTS

CROSS-REFERENCE TO RELATED APPLICATIONS

This application is the U.S. national phase of International Application No. PCT/EP2023/054664 filed Feb. 24, 2023, which designated the U.S. and claims priority to EP 22305218.4 filed Feb. 25, 2022, the entire contents of each of which are hereby incorporated by reference.

The present invention relates to methods for purification, detection and quantification of residual PEI-based transfection reagents. The present invention is directed to a method for performing an acidic hydrolysis of a liquid mixture comprising a biological matrix and a polyethyleneimine (PEI)-based transfection reagent of general formula (I) as described herein, wherein the biological matrix comprises a recombinant virus or virus-like particles produced using the PEI-based transfection reagent, and wherein said acidic hydrolysis does not degrade the PEI-based transfection reagent. The present invention also relates to a method for purifying, detecting and/or quantifying a PEI-based transfection reagent of general formula (I) as described herein.

Gene therapy aims to provide an exogenous gene in a cell to correct the expression of a deficient gene in monogenic diseases or to provide a new beneficial gene expression in cancer, viral and immune infections. To achieve that, an exogenous genetic material must be introduced efficiently into the cell correcting where the gene expression will trigger the expected therapeutic effect.

The exogenous genetic material consists of a gene expression system comprising the gene of interest framed by sequences controlling its expression (promoters, enhancer, exon, etc.) and presents on a nucleic acid construct (plasmid, DNA linear or ligated double-stranded, messenger RNA, etc.).

As eukaryotic cells are not permeable to nucleic acids, delivery systems or vectors allowing their introduction have been developed. Several systems based on viral or non-viral vectors are potent delivery systems. Therefore, among them, viral vectors represent the majority of delivery systems used in clinical applications.

Viral vectors have exploited the ability of viruses to target cells, in particular to infect cells, with great efficiency linked to biological evolution for millions of years. Taking advantage of their efficiency, viral vectors, in particular recombinant viral vectors have been constructed to maintain their capacity for cell targeting or infection but suppressing their pathogenicity while using them as a genomic sequence transporter. Among the recombinant viral vectors, AAVs, retroviruses, lentiviruses and adenoviruses are the most used in gene and cell therapy. This list is not exhaustive (for review, see '*Viral Vectors in Gene Therapy*', Kenneth Lundstrom, *Diseases* 2018, 6, 42) and depends on the progress and knowledge of other viruses and their potential use as a non-pathogenic genomic expression vector.

Viral vectors, in particular recombinant viral vectors are produced in cellular systems allowing their reproduction and multiplication, while avoiding the generation of wild type virus (for reviews, see Forsberg et al., *Key Considerations in Gene Therapy Manufacturing for Commercialization,* 2018).

Several cellular systems are used such as HEK293 cells, HeLa cells, or insect cells for the production of recombinant viral vectors. The process consists in introducing in the cell the genetic material of the recombinant virus necessary for the replication of its recombinant genome, the production of viral capsids and the encapsidation of the recombinant viral genome in its capsids, then for the recovery of the viral vectors produced.

Several methods are available to introduce the different components necessary for the production of a recombinant virus such as infection by baculovirus, transfection by chemical method (calcium phosphate or transfection reagent or formulation), physical method such as electroporation, or even generation of a stable cellular clone (integration into the host genome of the producing cell of the various viral genomic parts necessary for the production of the recombinant viruses).

The transfection by chemical method represents the method mainly used to produce the viruses used in gene and cell therapy, in particular AAVs or lentiviruses. The use of the calcium phosphate precipitation method, unsuitable for large-scale productions (production volume) due to the difficulty of controlling and reproducing nucleic acid precipitation, has been supplanted by the use of transfection reagent such as cationic polymers or cationic lipids. Among the cationic polymers, the PEI polymer is widely used for the production of recombinant viral vectors from HEK293 cells and derivatives.

Transfection allows the introduction of different nucleic acids, usually in the form of plasmid(s) as gene expression vectors into the cells necessary for the production of a recombinant virus. Transfection allows the introduction of viral genes and their transient expression over a few days (1 to 7 days) in virus-producing cells.

Several methods of polyethyleneimine's detection have been developed using spectrophotometric (Francesca Ungaro, et al. *J. Pharm. Biomed. Anal.* 31 (2003) 143), colorimetric (Qu, Fei Li, et al. *Langmuir* 2013, 29, 1199-1205) or fluorescent (Yunyi Zhang, et al. *Analytical and Bioanalytical Chemistry* 2017, 409, 4771) methods. These methods, based on specific interaction between PEI and metals (Copper, silver) (Yu Ling, et al. *J. Phys. Chem. C* 2015, 119, 27173-27177) are applicable to a solution which are not containing others nitrogen atoms able to chelate metals. These tests requiring extracting PEI from the sample matrix are not adapted to a composition comprising viral vectors, as some residual transfection reagent may be trapped inside virus.

The cells producing recombinant viruses are essentially HEK293 cells, their derivatives, subclones or genetically modified or other cells such as HeLa, CHO, . . . . These cells can be cultured either adherent or non-adherent (in suspension) in variable culture systems, on plastic or glass supports, or in bioreactor systems.

Virus-producing cells are cultured in culture media containing serum or not, proteins, peptides, vitamins, hormones, amino acids, lipids, salts, or containing various synthetic compounds without animal origin, or containing synthetic components, such as polymers or substances allowing their proliferation and good viability and avoiding their aggregation. Culture media are well-known, and examples of compositions are described in the literature, for example in Srivastava A, et al. (*J Pharm Sci.* 2021 July; 110(7):2609-2624).

The first successes of gene and cell therapy have made it possible to broaden viral vectors applications from rare diseases to more common diseases. Regulatory agencies are adapting their guidelines of manufacturing to this new offer. The methods and processes for producing viral vectors must be governed by rules to guarantee the patient safety. Regulatory agencies have put in place "guidelines" for the production of these new drugs concerning several aspects, safety, identity, quality, purity, impurity and potential of the substance (*WHO good manufacturing practices for biological products Replacement of Annex* 1 *of WHO Technical Report Series*, No. 822). Among these, the production process of the active substance comprising or consisting of the viral vector must be under control in terms of impurity and must be able to identify and quantify them if they can represent a safety risk.

The production of viral vectors by a transient transfection method in cells such as HEK293 cells or its derivatives consists of two phases. The introduction of nucleic acids encompassing viral and optionally additional genes (in the form of plasmids, 1 to 4 plasmids or other forms of gene expression vectors) into HEK293 cells, cultured under adherent or non-adherent conditions, in a synthetic culture medium or not, containing culture supplements, allows the production of recombinant viruses, whether or not excreted depending on the type of recombinant virus produced. This recombinant virus production step is referred to as an upstream process. It is followed by a step of harvesting the virus and then its purification until until it may be suitable for use as a drug active susbstance [Drug substance (DS) or Drug product (DP)] in a process of formulation of a drug composition, which is defined as the downstream process (J. Fraser Wright, *Biotechnology Journal,* 2021, 16, 2000022; Martinez-Molina et al., *Pharmaceutics* 2020, 12(11), 1051; and Christopher Perry and Andrea C. M. E. Rayat, *Viruses* 2021, 13, 268). At this final stage of production, additives such as acceptable pharmaceutical excipients or ingredients (*US Food and Drug Administration's* (*FDA's*) 21 *CFR* 210.3(*b*)(8) *guidance, an excipient or inactive ingredient is any component of a drug product other than the active ingredient, and EMEA Guideline on excipients in the dossier for application for marketing authorisation of medicinal product*, Doc. Ref. EMEA/CHMP/QWP/396951/2006) can be added to promote good conservation of the virus or to prevent its degradation or aggregation.

In this viral vector production process, the transfection reagent is a raw material in the upstream process which becomes a potential impurity in the final product (DS or DP) if it is not eliminated during the downstream process. The transfection reagent has hence to be identified and quantified throughout the upstream and downstream processes or in the final product (DS or DP). To date, there are no guidelines for acceptable doses of residual transfection reagent in virus preparations. However, the measurement of the residual rate seems to be obligatory to inform the regulatory production files and to have a traceability on the residual impurities in a viral preparation for therapeutic purposes which could represent a risk of toxicity.

An increasing demand for viral vectors is required to meet the expected need at the commercial level as well as the need generated by the rapid progression through the various phases of clinical development (Van Der Loo—*Human Molecular Genetics* 2015). Consequently, the development of large-scale production, new producer cell lines, new synthetic media or new transfection reagents are under investigation to increase the viral vector productivity at the upstream level.

Recently, new transfection reagents based on heterocyclic compounds grafted to cationic polymers have shown improved production yields of viral vectors including AAV and lentiviruses when compared to production achieved with PEI, considered as the gold standard transfection reagent (WO2021/023796; WO2021/023798). However, the assay (sometimes designated "residual assay" or "residual test") for residual contents of these new transfection reagents in the yielded viral vectors or during the processes for their production is not yet available.

Thus the aim of the invention is to develop a specific method able to determine the amount of a material in a complex liquid mixture. This material is present in very low quantity in a liquid mixture which further comprises a biological matrix. The biological matrix comprises a recombinant virus and/or virus-like particles and may be a cell culture medium, a buffer or any solution used during both the upstream (UP) and downstream process generating at the end a final drug substance. The material, by definition a transfection reagent, is used to produce viral vector (AAV, LV, Adenovirus, oncolytic virus, baculovirus) in mammalian cells. Following the production of the viral vector (upstream process), several steps are required to eliminate all the impurity generated during the UP to finally obtain a pure drug active ingredient which could be administered to a patient.

Several residual tests have to be performed to ensure the patient safety. One of them concerns the transfection reagent. The transfection reagent contains usually a cationic polymer or lipid. Due to their cationic properties, these reagents have the capacity to interact with nucleic acids but also with many other chemicals (polymers, salts, small molecules, etc.) used in the whole production process of viral vectors.

To ensure that the level of these transfection reagents is restrained within safe amounts, the regulatory institutions in the field require the development of analytical methods able to detect and quantify such residuals.

The inventors had to consider several criteria to develop an accurate residual test:

According to the biosafety level of the viruses, a preliminary virus inactivation step may be necessary to protect the manipulators. The inactivation step may be thermal (heating), chemical (detergents, acids, etc.) or physical (UV) and can generate by-products which could react with the transfection reagent. The choice of inactivation needs to be inefficient on the transfection reagent, i.e., needs to preserve the transfection reagent in the tested mixture that will be analyzed at the end.

Moreover, as the transfection reagent could stick to or be encapsulated into the virus, in the assay for residual contents of the transfection reagent the virus should be fully degraded to give access to this potentially encapsulated reagent.

At each step of the viral vector manufacturing process, the transfection reagent is present in a very low level compared to the other components (viruses, cell culture media, detergents, salts, etc.). The difficulty here is to detect this molecule into a complex liquid mixture. A specific purification step is needed to detect and quantify the residual transfection reagent. Considering this reagent is a macromolecule as are DNA, proteins of the virus, detergents used in the manufacturing or in the final formulation, a purification by size exclusion would not be accurate enough to allow a satisfying LOD (Limit of Detection) and LOQ (Limit of Quantification).

The sensitivity of the analytical method requires a large range of detection capability, from 1 ppm (LOD) to 1000 ppm, which could correspond to the amount of transfection reagent in the concentration phase of the downstream process.

Because each viral vector manufacturing process is unique, it is difficult to anticipate the impact of a viral vector composition on the analytical test. To simplify and develop a residual test that would generalize to viral vector manufacturing, the inventors decided to focus their attention on the development of an orthogonal degradation which will not affect the transfection reagents of general formula (I) as described herein (FIG. 1), which are well known for their transfection efficiency (Thomas Lorson, et al. Biomaterials 178 (2018) 204e280; Ts. Ivanova, E et al. PHARMACIA, 2016 vol.. 63, 3; Nico Adams, et al. Reviews 59 (2007) 1504-1520) .

Figure 2:
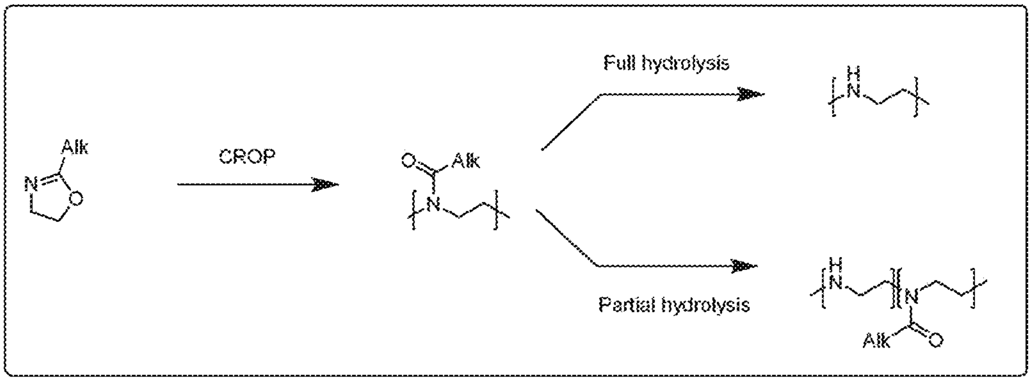
FIG. 2. Synthesis of PEI by CROP.

PEI derivatives represent a large family of polymers used for nucleic acids delivery (DNA, siRNA, mRNA, miRNA, etc) . In particular, linear PEIs (or lPEI) have shown strong transfection efficiency in both in vitro and in vivo applications. The synthesis of linear PEIs is based on a Cationic Ring Opening Polymerization (or CROP) of 2-alkyl-2-oxazolines generating polyalkyl-(2-oxazoline)s. Then, the polyalkyl-(2-oxazoline)s can be fully or partially hydrolyzed to generate lPEI or a combination of lPEI and polyalkyl-(2-oxazoline)s (Ryuichi Tanaka, et al. Macromolecules 1983, 16, 6, 849-853) (FIG. 2) .

Usually, the hydrolysis, which consists of a carbon-nitrogen bond cleavage of an amide's function, is performed under strong acidic conditions (Emi Haladjova, et al. *Polymers* 2020, 12, 2609; Alexander B. Cook, et al. *Polym. Chem.,* 2019, 10, 1202-1212; Emi Haladjova, et al. *Macromol. Biosci.* 2018, 1700349). Rangelov et al. performed partial degradation of poly(2-methyl-2-oxazoline) by an acidic hydrolysis at 100° C. in an aqueous solution containing 17.5% of HCl (Haladjova E, et al. *J Appl Polym Sci.* 2020; e49400; R. Shah, et al., *J. Mater. Sci. Mater. Med.* 2015, 26, 157). Heating time and degree of hydrolysis were directly correlated. Between 15 to 180 min at 100° C., the degree of hydrolysis (DH) increased from 2-6% up to 60% (Table 1).

TABLE 1

Influence of heating time.

| Polymer | k ($s^{-1}$) | DH for different time of hydrolysis (%) 15 min | 30 min | 60 min | 120 min | 180 min |
|---|---|---|---|---|---|---|
| PETOx-7.8k | $6.8 \times 10^{-5}$ | 6 | 10 | — | 38 | 53 |
| PETOx-9.6k | $8.5 \times 10^{-5}$ | 4 | 10 | 33 | 46 | 60 |
| PETOx-19.6k | $5.9 \times 10^{-5}$ | 2.5 | 4 | 14 | 30 | 59 |
| PETOx-Py-35.8k | $7.5 \times 10^{-5}$ | 2.6 | 6 | 14 | 41 | 60 |

Park et al. carried out at 100° C. for 6 h partial degradation of poly(2-ethyl-2-oxazoline) with various concentration of HCl (Ji Hoon Jeong, et al. *Journal of Controlled Release* 73 (2001) 391-399; R. Tanaka, et al., *Macromolecules* 16 (1983) 849-853). In this study, different concentrations of 5.0, 7.5, and 10.0% (v/v) HCl were used for the hydrolysis.

As the concentration of HCl increased, the extent of hydrolysis increased as listed in Table 2.

TABLE 2

Influence of HCl concentration.
Acid hydrolysis of poly(2-ethyl-2-oxazoline) at 100° C.

| Code | MW of poly(2-ethyl-2-oxazoline) | HCl concentration (%, v/v) | Percent hydrolysis[a] |
|---|---|---|---|
| A | 50 000 | 5.0 | 52.6 |
| B | 50 000 | 7.5 | 73.3 |
| C | 50 000 | 10.0 | 88.0 |
| D | 200 000 | 10.0 | 91.6 |

[a]Determined by using 400-MHz $^1H$ NMR spectra.

Figure 1:
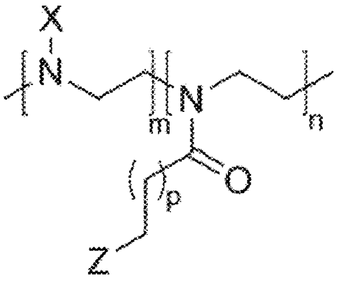
FIG. 1. Transfection reagent of general formula (I) .

Knowing that similar acid conditions can be applied to the degradation of nucleic acids or proteins or main components of viral vectors, the inventors have studied the conditions of degradation by acidic hydrolysis of the viral vectors contained in a biological matrix made up of various components present during the manufacture, purification and storage of viral vectors. Several parameters have been studied such as the source and concentration of acid, temperature, heating time to design a general method capable of specifically degrading a viral vector or any amide function except those included in the transfection reagents based on the general formula (I) (FIG. 1) .

The inventors provide a test able to detect and quantify PEI-based transfection reagents in a liquid mixture which comprises a biological matrix comprising recombinant viruses or virus-like particles and including the following steps:

- Optionally a viral vector inactivation,
- A specific acidic hydrolysis, which degrades a viral vector or any amide function except those of the PEI-based transfection reagents of general formula, i.e., said specific acidic hydrolysis does not affect PEI-based transfection reagents,
- A purification step able to separate PEI-based transfection reagents from by-products generated by the acidic hydrolysis,
- A qualitative and quantitative analysis of the residual PEI-based transfection reagents.

The method developed by the inventors shows several benefits. The method includes a purification of the transfection reagent meaning the analysis is specific, highly sensitive, robust and not dependent on sample composition. The method is applicable to different virus types or subtypes, at various concentrations and fully independent of the virus biosafety level. The method is not to be modified by the biological matrix nature (buffer, detergent, pH, etc.). The method is easily handled and may be used for research and development, clinical or commercial samples. The method may be GMP (good manufacturing practice) grade qualified.

Thus it is an object of the present invention to provide a method for performing an acidic hydrolysis of a liquid mixture comprising a biological matrix and a polyethyleneimine (PEI)-based transfection reagent,

- wherein the biological matrix comprises a recombinant virus or virus-like particles produced using the PEI-based transfection reagent,
- wherein the method comprises the step of incubating the liquid mixture comprising the biological matrix in an aqueous solution comprising from 0.1% to 10% (v/v) hydrochloric acid (HCl) at a temperature ranging from 60° C. to 110° C. for a time period ranging from 2 hours to 24 hours, preferably an aqueous solution comprising 0.1% (v/v) HCl at a temperature of 110° C. for 2 hours or in an aqueous solution comprising 1% (v/v) HCl at a temperature ranging from 60° C. to 80° C. for 2 hours, wherein said acidic hydrolysis does not degrade the PEI-based transfection reagent, and wherein the PEI-based transfection reagent is of general formula (I) or an acceptable salt thereof:

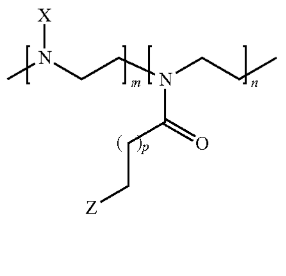

(I)

wherein:

m represents an integer between 27 to 1200, preferably an integer between 200 to 600, and n represents an integer between 3 to 600, preferably an integer between 20 to 300, with the proviso that n is lower than m and the sum of m+n ranges from 30 to 1200, X represents H or a group of formula:

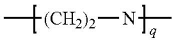

in which q represents an integer between 10 and 800, preferably 20 and 400, p represents an integer between 1 and 4, Z represents a group of formula:

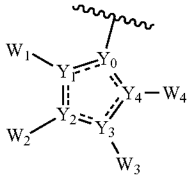

$Y_0$, $Y_1$, $Y_2$, $Y_3$ and $Y_4$, which may be identical or different, represent C or N, with the proviso that at least two, but no more than three, of $Y_0$, $Y_1$, $Y_2$, $Y_3$ and $Y_4$, are N, $W_1$, $W_2$, $W_3$ and $W_4$, which may be identical or different, represent H, a linear or branched, saturated or unsaturated $C_1$-$C_{18}$ alkyl, $C_6$-$C_{18}$ aryl, a linear or branched, saturated or unsaturated $C_6$-$C_{18}$ aryl-$C_1$-$C_{18}$ alkyl, $C_5$-$C_{10}$ heteroaryl, a linear or branched, saturated or unsaturated $C_2$-$C_{18}$ heteroalkyl, an amine, a linear or branched, saturated or unsaturated $C_1$-$C_{18}$ alkylamine, a $C_1$-$C_{12}$ alkoxy; or (i) $W_1$ and $W_2$ or (ii) $W_2$ and $W_3$ or (iii) $W_3$ and $W_4$ together form a fused, optionally substituted six-membered aryl; or a fused, optionally substituted six-membered heteroaryl containing no more than 1 N atom, with the proviso that at least one, but no more than two, of $W_1$, $W_2$, $W_3$ and $W_4$ is, or are, absent.

As defined herein, the term "$C_1$-$C_{18}$ alkyl" represents any monovalent radical of a linear or branched hydrocarbon chain comprising 1 to 18 carbon atoms. Examples of suitable $C_1$-$C_{18}$ alkyl groups include, but are not limited to, $C_1$-$C_4$ alkyl groups such as methyl, ethyl, n-propyl, i-propyl, n-butyl, i-butyl, s-butyl or t-butyl, $C_6$-$C_8$ alkyl groups such as n-hexyl, n-heptyl or n-octyl, as well as n-pentyl, 2-ethylhexyl, 3,5,5-trimethylhexyl, n-nonyl, n-decyl, n-undecyl, n-dodecyl or n-octadecyl.

As defined herein, the term "$C_6$-$C_{18}$ aryl" represents any monovalent radical of an aromatic hydrocarbon comprising 6 to 18 carbon atoms. Examples of suitable $C_6$-$C_{18}$ aryl groups include, but are not limited to, phenyl, naphthyl, anthracenyl or phenanthrenyl.

As defined herein, the term "$C_6$-$C_{18}$ aryl-$C_1$-$C_{18}$ alkyl" represents an aryl group as defined herein combined to an alkyl group as defined herein. Examples of suitable $C_6$-$C_{18}$ aryl-$C_1$-$C_{18}$ alkyl groups include, but are not limited to, benzyl, phenylethyl (or phenethyl), phenylpropyl, phenylbutyl, phenylpentyl, phenylhexyl, naphthylmethyl, naphthylethyl, naphthylpropyl, naphthylbutyl, naphthylpentyl, naphthylhexyl, anthracenylmethyl, anthracenylethyl, anthracenylpropyl, anthracenylbutyl, anthracenylpentyl, anthracenylhexyl, phenanthrenylmethyl, phenanthrenylethyl, phenanthrenylpropyl, phenanthrenylbutyl, phenanthrenylpentyl or phenanthrenylhexyl.

As defined herein, the term "$C_5$-$C_{10}$ heteroaryl" represents any monovalent radical of a monocyclic or bicyclic 5 to 10 membered aromatic group comprising from 1 to 3 heteroatoms independently selected from oxygen, nitrogen and sulfur. Examples of suitable $C_5$-$C_{10}$ heteroaryl groups include, but are not limited to, furyl, thienyl, pyrrolyl, pyrazoyl, imidazolyl, isoxazolyl, isothiazoyl, thiazolyl, oxazolyl, 1,2,3-triazolyl, 1,2,4-triazolyl, 1-benzofuryl, 1-benzothienyl, indolyl, benzimidazolyl, indazolyl, 1,2-benzisoxazolyl, 2,1-benzisoxazolyl, 1,2-benzisothiazolyl, 2,1-benzisothiazolyl, benzothiazolyl, benzoxazolyl, benzotriazolyl, pyridyl, pyridinium, quinolinyl, quinolinium, isoquinolinyl, isoquinolinium, pyridazinyl, cinnolinyl, phthalazinyl, pyrimidinyl, quinazolinyl, pyrazinyl or quinoxalinyl.

As defined herein, the term "$C_2$-$C_{18}$ heteroalkyl" represents an alkyl group as defined herein substituted by one or more heteroatoms such as O, N, or S.

As defined herein, the term "$C_1$-$C_{18}$ alkylamine" represents any monovalent radical of a linear or branched hydrocarbon chain comprising 1 to 18 carbon atoms, in which one of the hydrogen atom bonded to a carbon atom is replaced by an amino group. Examples of suitable $C_1$-$C_{18}$ alkylamine include, but are not limited to, $—(CH_2)_n—NH_2$, with n representing an integer between 1 and 18, $—CH_2NHCH_3$, $—CH_2CH(CH_3)—NH_2$, or $—(CH_2)_nN(CH_3)_2$, with n representing an integer between 1 and 6.

As defined herein, the term "$C_1$-$C_{12}$ alkoxy" represents a radical of formula —OR', wherein R' is a $C_1$-$C_{12}$ alkyl. Examples of suitable $C_1$-$C_{12}$ alkoxy groups include, but are not limited to, $C_1$-$C_6$ alkoxy groups such as methoxy ($—OCH_3$), ethoxy ($—OCH_2CH_3$), t-butoxy ($—OC(CH_3)_3$), or $—O(CH_2)_5CH_3$.

Unless mentioned otherwise, the groups and radicals defined hereinabove may be unsubstituted or substituted by one or more substituents such as, for example, halogen, alkyl, alkoxy, aryl, heteroaryl, haloalkyl, haloalkoxy, alkoxycarbonyl, alkanoyl, aroyl, formyl, nitrile, nitro, amido, alkylthio, alkylsulfinyl, alkylsulfonyl, arylthio, arylsulfinyl, arylsulfonyl, amino, alkylamino, arylamino, dialkylamino and diarylamino.

As defined herein, the term "halogen" represents an atom of F, Cl, Br or I.

In a particular embodiment of the invention, the PEI-based transfection reagent of general formula (I) as defined herein is one wherein $W_1$, $W_2$, $W_3$ and $W_4$, which may be identical or different, represent H, methyl, cyclopropyl, isopropyl, tert-butyl, phenyl, benzyl, 2-pyridine, 3-pyridine, or 4-hydroxyphenethyl; or wherein (i) $W_1$ and $W_2$ or (ii) $W_2$ and $W_3$ or (iii) $W_3$ and $W_4$ together form a fused phenyl; a fused phenyl substituted by a methyl group, in particular two methyl groups, a methoxy group, a carboxyphenyl or Cl; a fused naphthalene; a fused 2-pyridine; or a fused 3-pyridine.

In a particular embodiment of the invention, the PEI-based transfection reagent of general formula (I) as defined herein is one wherein X represents a branched PEI, which is a group of formula:

$$-\!\!\left[(CH_2)_2-N\right]_q\!-,$$

in which q represents an integer between 10 and 800, preferably 20 and 400.

Examples of branched PEIs are well known to the person skilled in the art.

In a preferred embodiment of the invention, the PEI-based transfection reagent of general formula (I) as defined herein is one wherein X represents H, i.e. X is a linear PEI. Examples of linear PEIs (IPEIs) are well known to the person skilled in the art.

In a particular embodiment of the invention, the PEI-based transfection reagent of general formula (I) as defined herein has a grafting ratio defined as (n/(m+n))*100, wherein the grafting ratio is ranging from 1 to 50%, preferably from 5 to 30%, more preferably is 20%.

As defined herein, the term "grafting ratio" refers to the number of grafted monomer units on primary or secondary amino groups by side chains, divided by the number of total monomer units present in an original cationic polymer backbone (i.e., the PEI polymer backbone). The grafting ratio will depend upon the molecular weight of the cationic polymer, the chemical reactivity of the grafted side chains onto the polymer, or the obtained biological effect. Said grafting ratio may be determined by a measurement method well known in the art, for example by NMR.

The PEI polymer backbone is of general formula (II):

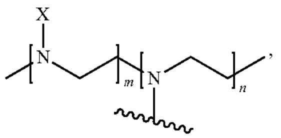

wherein $m$, $n$ and X are as defined herein.

In a particular embodiment of the invention, the PEI polymer backbone has an average molecular weight (Mw) ranging from 1 kDa to 50 kDa, preferably from 5 kDa to 30 kDa or from 10 kDa to 25 kDa, more preferably the PEI polymer backbone has an average molecular weight (Mw) of 8, 10, 15, 22, 25 or 30 kDa, preferably of 22 kDa.

In a particular embodiment of the invention, in the general formula (I) of the PEI-based transfection reagent, the sum of m+n ranges from 30 to 1200, preferably from 200 to 600, and the average molecular weight (Mw) of the PEI polymer backbone ranges from 1 kDa to 200 kDa, in particular from 1 kDa to 50 kDa, preferably from 5 kDa to 30 kDa or from 10 kDa to 25 kDa, more preferably is of 8, 10, 15, 22, 25 or 30 kDa, even more preferably of 22 kDa.

In a particular embodiment of the invention, m represents an integer between 27 to 600 and n represents an integer between 3 to 600. Preferably, m represents an integer between 198 to 300 and n represents an integer between 2 to 300.

In another particular embodiment of the invention, the sum of m+n ranges from 30 to 1200, preferably from 200 to 600.

In a preferred embodiment of the invention, the PEI polymer backbone has an average molecular weight (Mw) of 8, 10, 15, 22, 25 or 30 kDa, preferably of 22 kDa. When the average molecular weight (Mw) of the PEI polymer backbone is 8, 10, 15, 22, 25 or 30 kDa, the sum of m+n is equal to 180, 220, 340, 500, 570 or 680 respectively.

In preferred embodiment of the invention, the PEI-based transfection reagent of general formula (I) is selected from the group consisting of the following compounds:

Compound 01

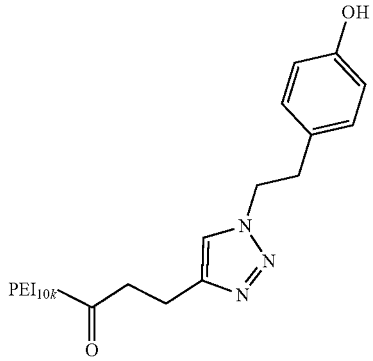

-continued
Compound 02
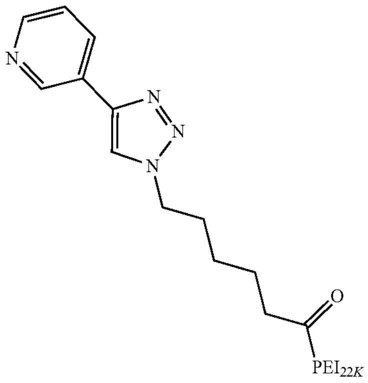
Compound 03
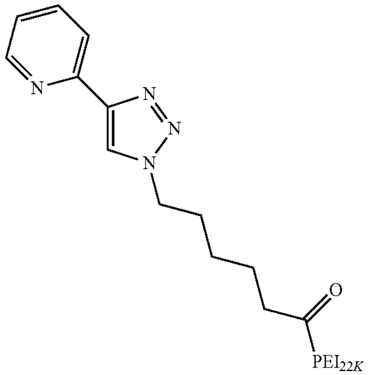
Compound 04
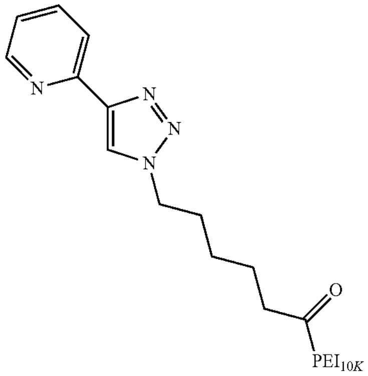
Compound 05
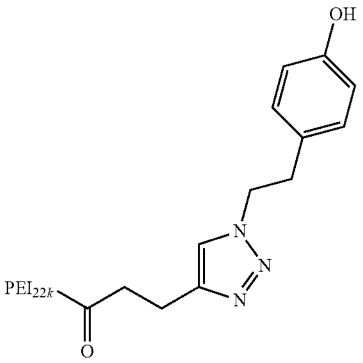

-continued
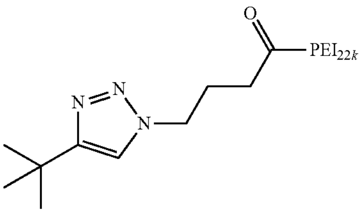
Compound 06
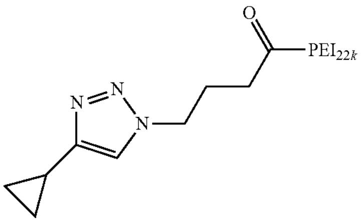
Compound 07
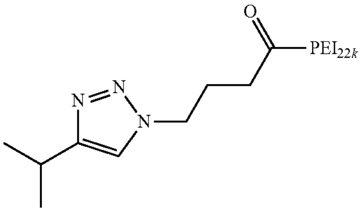
Compound 08
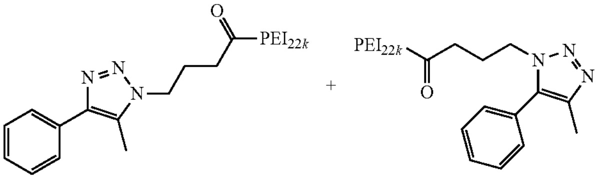
Compound 09
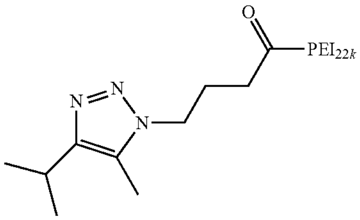
Compound 10
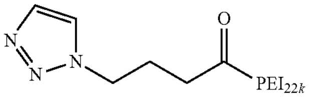
Compound 11
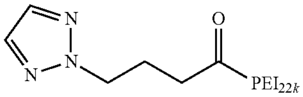
Compound 12
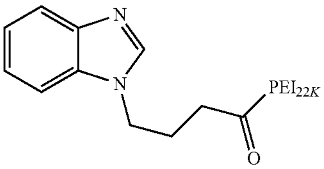
Compound 13

-continued
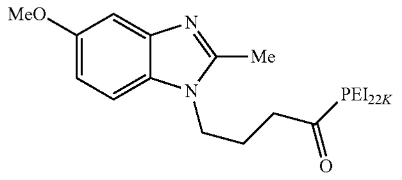
Compound 14
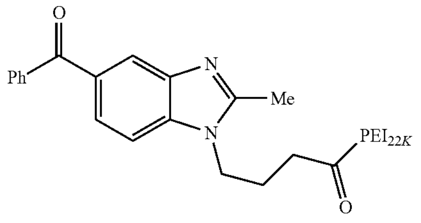
Compound 15
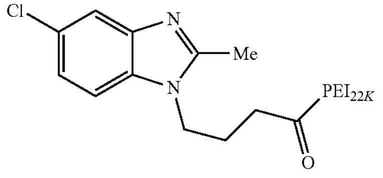
Compound 16
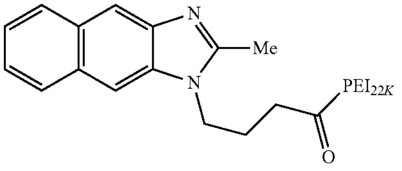
Compound 17
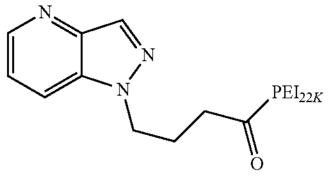
Compound 18
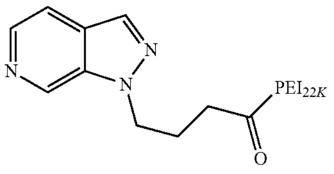
Compound 19
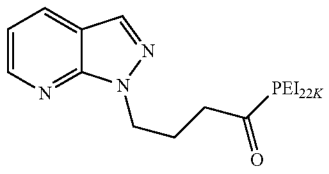
Compound 20
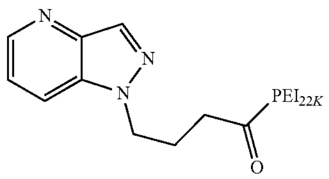
Compound 21

-continued
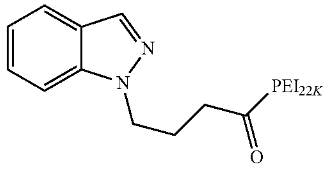
Compound 22
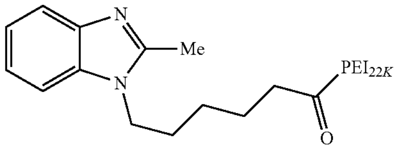
Compound 23
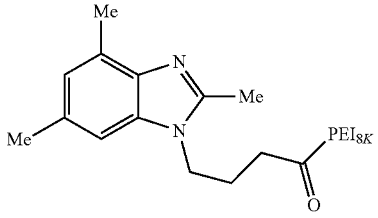
Compound 24
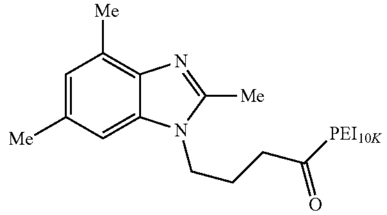
Compound 25
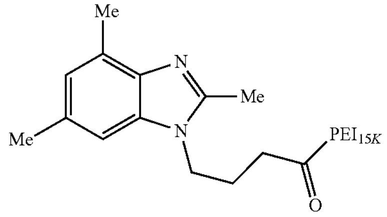
Compound 26
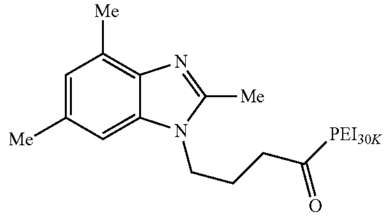
Compound 27
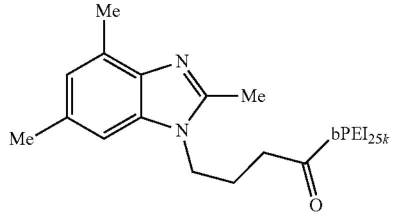
Compound 28

-continued

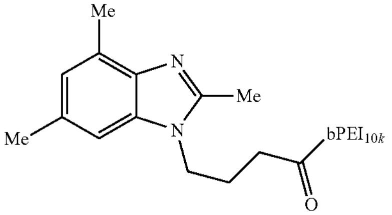

Compound 29

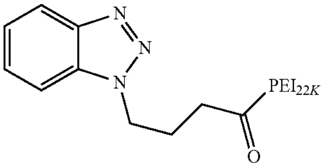

Compound 30

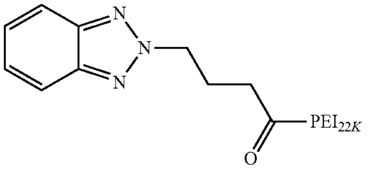

Compound 31

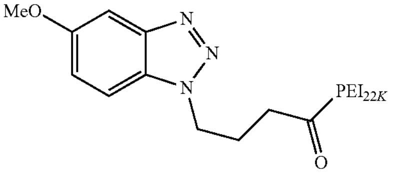

Compound 32

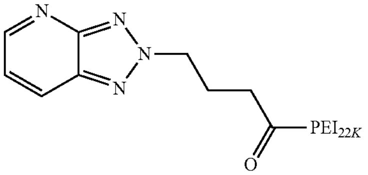

Compound 33

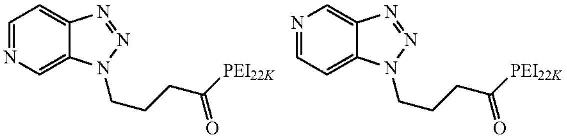

Compound 34

In these compounds 1-34, the term "PEI" refers to a linear PEI, and the term "bPEI" refers to a branched PEI.

The compound of general formula (I) may be prepared according to various methods well known in the art, for example as disclosed in the patent applications WO2021/023796 and WO2021/023798.

In a particular embodiment of the invention, the biological matrix is selected from the group consisting of a cell culture medium, in particular a culture medium of eukaryotic cells, in particular suspension cells or adherent cells, a buffer, a solution used during the manufacturing and purification process of recombinant viruses, and a final composition comprising the purified viruses in a final formulation comprising pharmaceutically acceptable buffer and excipients.

As defined herein, the term "cell culture medium" has the meaning known in the art and refers for example to a medium containing at least one of the following components: serum, synthetic medium, animal-free component medium or chemically defined medium, in particular medium for maintaining cells alive, or for growing, for differentiating or for expanding cells, or for enhancing transfection.

As defined herein, the term "suspension cells" refers to cells that do not need solid support for growth and are thus anchorage-independent. Examples of suspension cells include, but are not limited to, NSO cells, U937 cells, Namalawa cells, HL60 cells, WEHI231 cells, Yac 1 cells, Jurkat cells, THP-1 cells, K562 cells or U266B1 cells.

As defined herein, the term "adherent cells" refers to cells that need solid support for growth and are thus anchorage-dependent. Examples of adherent cells include, but are not limited to, MRC-5 cells, HeLa cells, Vero cells, NIH-3T3 cells, L293 cells, CHO cells, BHK-21 cells, MCF-7 cells, A549 cells, COS cells, HEK 293 cells, Hep G2 cells, SNN-BE(2) cells, BAE-1 cells or SH-SY5Y cells.

As defined herein, the term "buffer" refers to a buffer solution comprising a buffering agent. As defined herein, the term "buffering agent" refers to an agent that adjusts, maintains or controls the pH of a solution. Buffering agents can be either the weak acid or weak base that would comprise a buffer solution. Examples of suitable buffering agents include, but are not limited to, sodium carbonate, sodium bicarbonate, sodium hydroxide, calcium bicarbonate, calcium citrate, sodium citrate, magnesium hydroxide, magnesium bicarbonate, potassium acetate, Tris acetate, sodium acetate, potassium phosphate monobasic, potassium carbonate, potassium bicarbonate, potassium citrate, or magnesium oxide.

As defined herein, the expression "a solution used during the manufacturing and purification process of recombinant viruses" refers to any solution well known in the art that can be used during the manufacturing and purification process of recombinant viruses.

As defined herein, the term "pharmaceutically acceptable buffer and excipients" refers to a pharmaceutically acceptable vehicle, which is any substance or combination of substances physiologically acceptable i.e., appropriate for its use in a composition in contact with a host (especially for administration to a host), especially a human, and thus non-toxic. It can refer to a solid, semi-solid or liquid filler, diluent, encapsulating material or formulation auxiliary of any conventional type. Examples of suitable acceptable excipients include, but are not limited to, glucose, galactose, lactose, dextrose, maltose, mannitol, sucrose, trehalose, polyethyleneglycol, or pluronic acid.

It is another object of the present invention to provide a method for purifying, detecting and/or quantifying a polyethyleneimine (PEI)-based transfection reagent of general formula (I) as defined herein, wherein the PEI-based transfection reagent of general formula (I) is comprised in a liquid mixture comprising a biological matrix, wherein the biological matrix comprises a recombinant virus or virus-like particles produced using the PEI-based transfection reagent of general formula (I), wherein the method comprises the steps of:

(a) performing an acidic hydrolysis of the liquid mixture according to the method of the invention, (b) purifying the reaction mixture obtained in step (a) in order to obtain a purified PEI-based transfection reagent of general formula (I), (c) detecting and/or quantifying the purified PEI-based transfection reagent of general formula (I) obtained in step (b).

As defined herein, the term "purifying" means that other constituents of the solution are separated or removed to keep the solution of the transfection reagent only.

In a particular embodiment of the invention, before performing step (a), the method comprises a step of inactivating the recombinant virus or virus-like particles by heating the biological matrix at a temperature ranging from 110° C. to 130° C. for a time period ranging from 30 minutes to 4 hours, preferably at a temperature of 120° C. for 30 minutes.

In a particular embodiment of the invention, step (b) is performed using ultrafiltration or centrifugation.

In a particular embodiment of the invention, step (c) is performed using High-performance liquid chromatography (HPLC) or Ultra high-performance liquid chromatography (UHPLC) analytical technique, preferably UHPLC.

In a particular embodiment of the invention, the PEI-based transfection reagent of general formula (I) of step (c) is detected with a limit of detection (LOD) ranging from 1 ppm to 1000 ppm, and/or a limit of quantification (LOQ) ranging from 1 ppm to 1000 ppm.

In a particular embodiment of the invention, the PEI-based transfection reagent of general formula (I) is detectable in a biological matrix during the manufacturing process of the recombinant viruses, wherein the biological matrix is selected from the group consisting of a cell culture medium, in particular a culture medium of eukaryotic cells, in particular suspension cells or adherent cells, a buffer, a solution used during the manufacturing and purification process of recombinant viruses, and a final composition comprising purified viruses in a final formulation comprising pharmaceutically acceptable buffer and excipients.

In another particular embodiment of the invention, the PEI-based transfection reagent is used during the manufacturing process of an advanced therapy medicinal product (ATMP) and is present in residual quantity (1 to 1000 ppm) with respect to transfection reagents provided in the manufacturing process and to other components of the liquid mixture.

The terms "cell culture medium", "suspension cells", "adherent cells", "buffer", "a solution used during the manufacturing and purification process of recombinant viruses" and "pharmaceutically acceptable buffer and excipients" are defined according to the above definitions and in accordance with examples provided herein.

In a particular embodiment of the invention, the recombinant virus is selected from the group consisting of an adeno-associated virus (AAV), a lentivirus (LV), an adenovirus, an oncolytic virus and a baculovirus, preferably is an adeno-associated virus (AAV) or a lentivirus (LV), more preferably is an adeno-associated virus (AAV).

In a particular embodiment of the invention, the PEI-based transfection reagent of general formula (I) is a compound selected from the group consisting of compounds 01, 02, 03, 04, 05, 06, 07, 08, 09, 10, 11, 12, 30, 31, 32, 33 and 34, and the recombinant virus is an adeno-associated virus (AAV).

Other features and advantages of the invention will be apparent from the examples which follow and will also be illustrated in the figures.

EXAMPLES

Example 1. General Procedure for the Preparation of Grafted Polymers

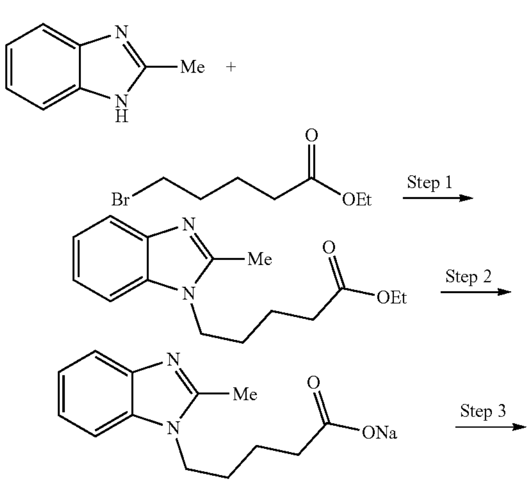

-continued

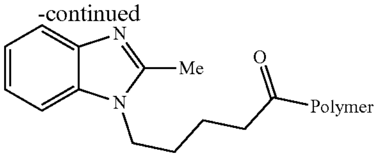

Step 1: N-Alkylation of Heterocycles

In an oven-dried round-bottom flask under argon was added the corresponding heterocycle (1 equiv.) and DMF (2 ml/mmol of starting material). The solution was cooled to 0° C. and Sodium Hydride (60% dispersion in mineral oil, 1.2 equiv.) was added by portion. The mixture was slowly warmed up to room temperature over 1 hour. Then, the corresponding ester was added dropwise and the reaction was stirred at room temperature for 4-12 hours. The mixture was quenched by addition of water (10 mL/1 mL of DMF) and the aqueous layer was extracted with EtOAc. (5×2 mL/1 mL of DMF). The combined organic extracts were washed with brine and dried over anhydrous $MgSO_4$. After filtration, the solvent was removed in vacuo and the resulting oil was purified by column chromatography (EtOAc 20 to 50% in heptane).

Step 2: Saponification of Acid Moieties

To a solution of ester in EtOH (2 mL/mmol of ester) was added dropwise a 5 M solution of NaOH (0.2 mL/mmol of ester), and the mixture was stirred at room temperature overnight. Then, the solvent was removed in vacuo and the residue was purified by column chromatography on $SiO_2$ using MeOH 5% in DCM+AcOH 1% or using Acetonitrile 0 to 100% in $H_2O$.

Step 3: Grafting

In a round-bottom flask was added the cationic polymer (1 equiv.) in water (4 mL/mmol of starting material) followed by N-methyl morpholine or NMM (2 equiv.). The carboxylate (0.3-1 equiv.) was added followed by MeOH (16 mL/mmol of polymer). After stirring 10 minutes, 4-(4,6-dimethoxy-1,3,5-triazin-2-yl)-4-methylmorpholinium chloride was added or DMTMM (0.6-2 equiv.) and the mixture was stirred 12-24 hours at room temperature. Then, MeOH was removed in vacuo, water (4 mL/mmol of starting material) followed by a solution of 3M HCl (1 mL/mmol of starting material) were added. The residue was purified using a dialysis cassette in a 50 mM HCl bath.

Step 4: Synthesis of Triazole by «Click» Chemistry Starting from an Acid.

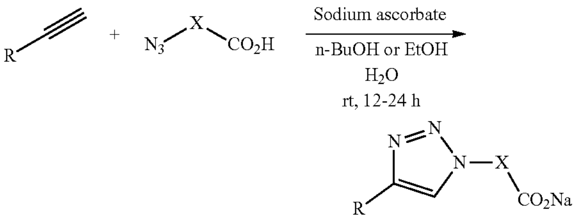

or

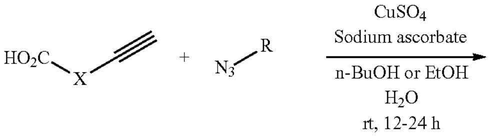

-continued

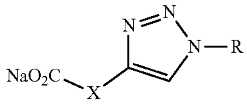

Alkyne (1 equiv.), azide (1 equiv.), $CuSO_4$ (0.01 equiv) and sodium ascorbate (0.03 equiv) were added to a 2:1 (v/v) solution of nBuOH and water. The reaction was stirred at room temperature for 24 hours. Then, NaOH (5 M, 2 equiv.) was added, and the organic solvent was removed in vacuo. The residue was purified by reversed phase flash chromatography using 0 to 100% $CH_3CN$ in water as eluant.

Step 5: Synthesis of Triazole by «Click» Chemistry Starting from an Ester

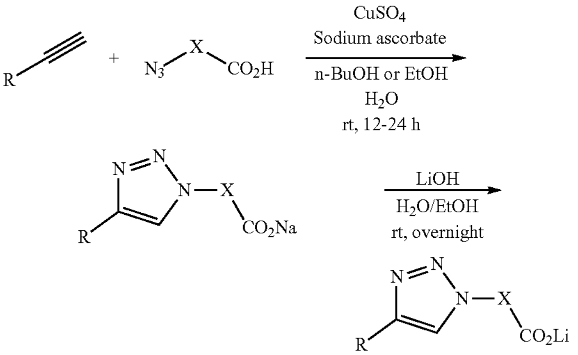

or

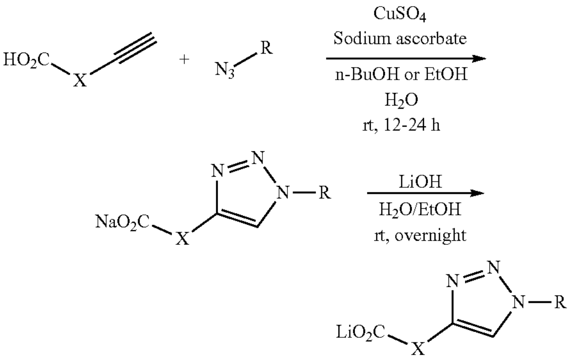

Alkyne (1 equiv.), azide (1 equiv.), $CuSO_4$ (0.01 equiv) and sodium ascorbate (0.03 equiv) were added to a 2:1 (v/v) solution of nBuOH and water. The reaction was stirred at room temperature for 24 hours. Then, NaOH (5 M, 2 equiv.) was added, and the organic solvent was removed in vacuo. The residue was purified by reversed phase flash chromatography using 0 to 100% $CH_3CN$ in water as eluant.

Step 6: Saponification of the Ester Moiety.

To a solution of ester in EtOH was added dropwise a 3 M solution of LiOH, and the mixture was stirred at rt for the weekend. Then, the solvent was removed in vacuo and the residue was purified by reverse phase FC on $SiO_2$ using $H_2O$/MeCN as eluant using a Biotage Flash purification system. The acid obtained was lyophilized to yield a solid.

Example 2. Syntheses of PEI-Based Transfection Reagents of the Invention

Synthesis of Compound 13 (Polymer Molecular Weight=22k, Heterocycle Grafting=10%)

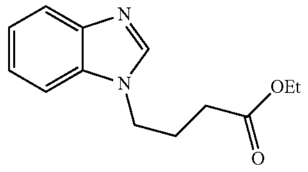 [SMILES: CCOC(=O)CCCn1cnc2ccccc21]

Intermediate 13.a was prepared analogously to the general procedure, step 1 (Example 1). Yield=60%; m=2.30 g; $^1$H NMR (400 MHz, Chloroform-d) δ 7.94 (s, 1H), 7.81-7.72 (m, 1H), 7.43-7.36 (m, 1H), 7.26 (ddd, J=13.1, 7.5, 4.9 Hz, 2H), 4.24 (t, J=7.0 Hz, 2H), 4.09 (q, J=7.4 Hz, 2H), 2.28 (t, J=7.0 Hz, 2H), 2.16 (p, J=7.0 Hz, 2H), 1.20 (t, J=7.1 Hz, 3H).

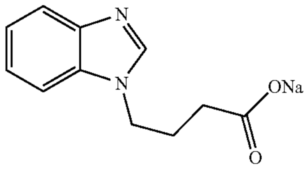

Intermediate 13.b was prepared analogously to the general procedure, step 2 (Example 1). Yield=45%; m=1.00 g; $^1$H NMR (400 MHz, Methanol-$d_4$) δ 8.21 (d, J=2.4 Hz, 1H), 7.70 (d, J=8.0 Hz, 1H), 7.63 (d, J=8.0 Hz, 1H), 7.33 (dt, J=17.3, 7.5 Hz, 2H), 4.37 (t, J=7.4 Hz, 2H), 2.35 (t, J=7.4 Hz, 2H), 2.18 (p, J=7.4 Hz, 2H).

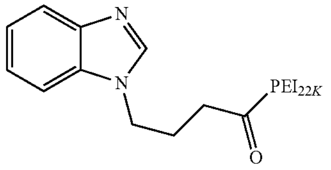

Compound 13 was prepared analogously to the general procedure, step 3 (Example 1). Yield=94%; m=117 mg; $^1$H NMR ($D_2O$) δ: $^1$H NMR (400 MHz, Deuterium Oxide) δ 9.29-8.97 (m, 1H), 7.96-7.17 (m, 4H), 4.46 (d, J=42.4 Hz, 2H), 3.45 (s, 39H), 2.35 (dd, J=135.3, 58.1 Hz, 4H).

Synthesis of Compound 14 (Polymer Molecular Weight=22k, Heterocycle Grafting=24%)

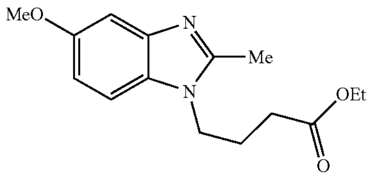

Intermediate 14.a was prepared analogously to the general procedure, step 1 (Example 1). Yield=63%; m=1.7 g; $^1$H NMR (400 MHz, Chloroform-d) δ 7.63 (d, J=8.7 Hz, 0H), 7.27 (d, J=8.8 Hz, 1H), 6.99-6.86 (m, 2H), 4.27-4.15 (m, 4H), 3.93 (dd, J=7.3, 1.3 Hz, 3H), 2.65 (dd, J=3.7, 1.3 Hz, 3H), 2.43 (q, J=6.8 Hz, 2H), 2.18 (p, J=7.1 Hz, 2H), 1.33 (td, J=7.2, 1.3 Hz, 3H).

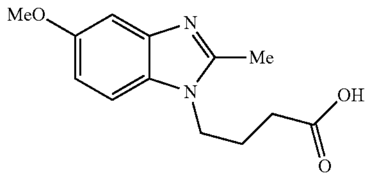 [SMILES: CCOC(=O)CCCn1c(C)nc2cc(OC)ccc21]

Intermediate 14.b was prepared analogously to the general procedure, step 2 (Example 1). Yield=100%; m=676 mg; $^1$H NMR (400 MHz, Methanol-$d_4$) δ 7.54 (dd, J=32.8, 8.9 Hz, 1H), 7.18 (dd, J=33.3, 2.4 Hz, 1H), 7.01 (ddd, J=21.3, 8.9, 2.3 Hz, 1H), 4.33 (q, J=6.8, 6.3 Hz, 2H), 3.92-3.84 (m, 3H), 2.70 (d, J=8.0 Hz, 3H), 2.43 (q, J=6.7 Hz, 2H), 2.12 (p, J=7.0 Hz, 2H).

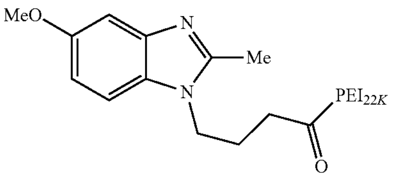

Compound 14 was prepared analogously to the general procedure, step 3 (Example 1). Yield=100%; m=175 mg; $^1$H NMR (400 MHz, Deuterium Oxide) δ 7.80-6.57 (m, 3H), 4.44-2.96 (m, 22H), 2.80-1.38 (m, 7H).

Synthesis of Compound 15 (Polymer Molecular Weight=22k, Heterocycle Grafting=27%)

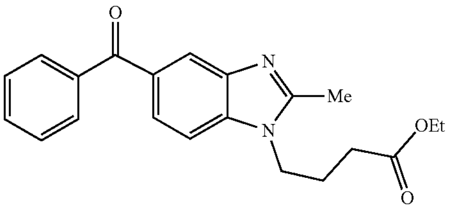 [SMILES: CCOC(=O)CCCn1c(C)nc2cc(C(=O)c3ccccc3)ccc21]

Intermediate 15a was prepared analogously to the general procedure, step 1 (Example 1). Yield=50%; m=820 mg; $^1$H NMR (400 MHz, Chloroform-d) δ 7.94-7.21 (m, 8H), 7.05 (d, J=1.3 Hz, 1H), 5.08 (d, J=1.3 Hz, 2H), 4.05 (td, J=8.1, 7.5, 2.9 Hz, 2H), 3.92 (dtd, J=16.2, 7.8, 6.5 Hz, 2H), 2.50 (dd, J=12.5, 1.4 Hz, 3H), 2.19 (q, J=6.3 Hz, 2H), 1.94 (p, J=7.0 Hz, 2H), 1.04 (ddd, J=14.3, 7.9, 6.5 Hz, 3H).

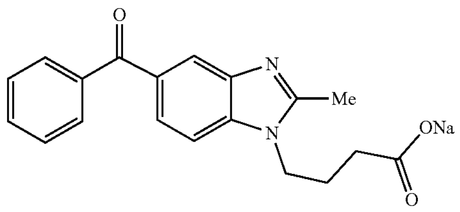

Intermediate 15.b was prepared analogously to the general procedure, step 2 (Example 1). Yield=73%; m=580 mg; $^1$H NMR (400 MHz, Methanol-$d_4$) δ 8.01 (d, J=8.9 Hz, 1H), 7.83-7.48 (m, 7H), 4.34 (tt, J=7.3, 3.0 Hz, 2H), 2.71-2.65 (m, 2H), 2.41 (ddt, J=10.2, 7.4, 4.2 Hz, 2H), 2.12 (h, J=7.2 Hz, 2H).

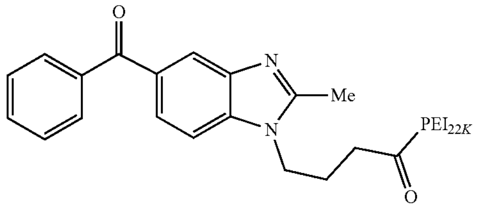

Compound 15 was prepared analogously to the general procedure, step 3 (Example 1). Yield=84%; m=171 mg; $^1$H NMR (400 MHz, Deuterium Oxide) δ 7.92-6.49 (m, 8H), 4.50-3.10 (m, 17H), 3.03-1.78 (m, 7H).

Synthesis of Compound 16 (Polymer Molecular Weight=22k, Heterocycle Grafting=30%)

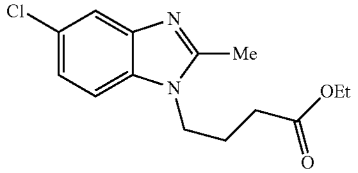 [SMILES: CCOC(=O)CCCn1c(C)nc2cc(Cl)ccc21]

Intermediate 16a was prepared analogously to the general procedure, step 1 (Example 1). Yield=91%; m=1.55 g; $^1$H NMR (400 MHz, Chloroform-d) δ 7.68-7.53 (m, 1H), 7.33-7.16 (m, 2H), 4.14 (pd, J=7.4, 1.6 Hz, 4H), 2.61 (d, J=1.5 Hz, 3H), 2.35 (td, J=6.9, 3.5 Hz, 2H), 2.09 (h, J=5.8, 4.7 Hz, 2H), 1.26 (tdd, J=6.9, 4.5, 1.5 Hz, 3H).

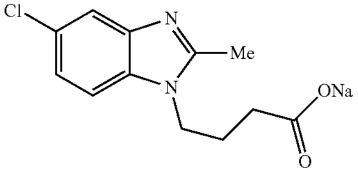

Intermediate 16b was prepared analogously to the general procedure, step 2 (Example 1). Yield=60%; m=840 mg; $^1$H NMR (400 MHz, Methanol-$d_4$) δ 7.85 (s, 1H), 7.75-7.60 (m, 1H), 7.45-7.38 (m, 1H), 4.39 (q, J=7.6, 6.5 Hz, 2H), 2.77 (t, J=2.9 Hz, 3H), 2.49 (t, J=6.6 Hz, 2H), 2.13 (p, J=7.3 Hz, 2H).

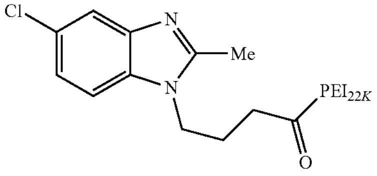

Compound 16 was prepared analogously to the general procedure, step 3 (Example 1). Yield=100%; m=193 mg; $^1$H NMR (400 MHz, Deuterium Oxide) δ 7.83-6.65 (m, 3H), 4.52-3.09 (m, 15H), 3.04-2.32 (m, 5H), 2.30-1.72 (m, 2H).

Synthesis of Compound 17 (Polymer Molecular Weight=22k, Heterocycle Grafting=26%)

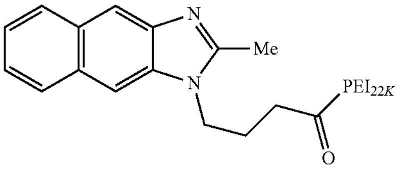

Compound 17 was prepared analogously to the general procedure, step 3 (Example 1). Yield=97%; m=198 mg; $^1$H NMR (400 MHz, Deuterium Oxide) δ 8.19-6.14 (m, 6H), 4.51-0.73 (m, 24H).

Synthesis of Compound 18 (Polymer Molecular Weight=22k, Heterocycle Grafting=47%)

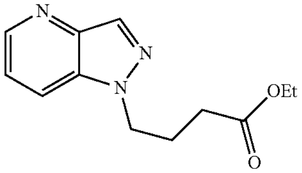 [SMILES: CCOC(=O)CCCn1ncc2ncccc21]

Intermediate 18a was prepared analogously to the general procedure, step 1 (Example 1). Yield=15%; m=211 mg; $^1$H NMR (400 MHz, Chloroform-d) δ 8.52 (dd, J=4.4, 1.3 Hz, 1H), 8.19 (d, J=1.0 Hz, 1H), 7.77 (dt, J=8.5, 1.2 Hz, 1H), 7.24 (dd, J=8.6, 4.4 Hz, 1H), 4.46-4.38 (m, 2H), 4.04 (q, J=7.2 Hz, 2H), 2.28-2.13 (m, 4H), 1.17 (t, J=7.1 Hz, 3H).

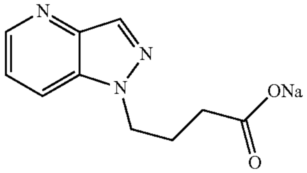

Intermediate 18b was prepared analogously to the general procedure, step 2 (Example 1). Yield=100%; m=887 mg; $^1$H NMR (400 MHz, Deuterium Oxide) δ 8.24 (dd, J=4.5, 1.3 Hz, 1H), 7.92 (d, J=1.0 Hz, 1H), 7.76 (dt, J=8.7, 1.2 Hz, 1H), 7.20 (dd, J=8.7, 4.4 Hz, 1H), 4.21-4.13 (m, 2H), 2.02-1.87 (m, 4H).

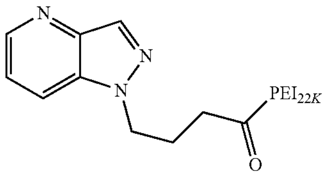

Compound 18 was prepared analogously to the general procedure, step 3 (Example 1). Yield=97%; m=103 mg; $^1$H NMR (400 MHz, Deuterium Oxide) δ 8.92-7.42 (m, 4H), 4.61-4.25 (m, 2H), 4.04-3.09 (m, 10H), 2.67-1.88 (m, 5H).

Synthesis of Compound 19 (Polymer Molecular Weight=22k, Heterocycle Grafting=25%)

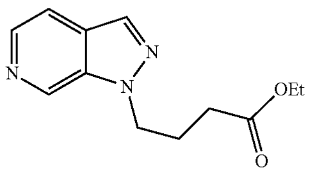 [SMILES: CCOC(=O)CCCn1ncc2ccncc21]

Intermediate 19a was prepared analogously to the general procedure, step 1 (Example 1). Yield=43%; m=602 mg; $^1$H NMR (400 MHz, Chloroform-d) δ 9.00 (s, 1H), 8.29 (d, J=5.6 Hz, 1H), 8.04 (d, J=0.8 Hz, 1H), 7.61 (dd, J=5.6, 1.3 Hz, 1H), 4.61-4.52 (m, 2H), 4.09 (q, J=7.1 Hz, 2H), 2.34-2.21 (m, 4H), 1.20 (t, J=7.1 Hz, 3H).

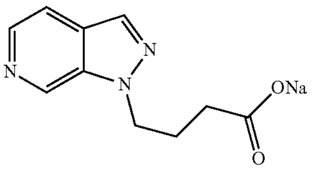

Intermediate 19b was prepared analogously to the general procedure, step 2 (Example 1). Yield=100%; m=592 mg; $^1$H NMR (400 MHz, Deuterium Oxide) δ 8.77 (s, 1H), 8.04-7.93 (m, 2H), 7.57 (dd, J=5.8, 1.3 Hz, 1H), 4.37-4.29 (m, 2H), 2.07-1.93 (m, 4H).

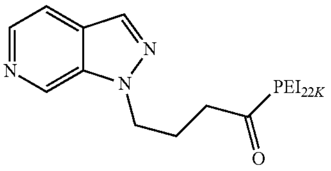

Compound 19 was prepared analogously to the general procedure, step 3 (Example 1). Yield=100%; m=84 mg; $^1$H NMR (400 MHz, Deuterium Oxide) δ 9.67-8.10 (m, 4H), 4.23-3.06 (m, 16H), 2.86-1.90 (m, 4H).

Synthesis of Compound 20 (Polymer Molecular Weight=22k, Heterocycle Grafting=22%)

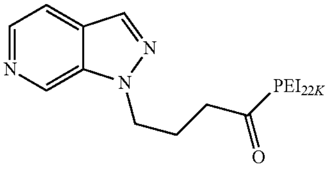

Compound 20 was prepared analogously to the general procedure, step 3 (Example 1). Yield=89%; m=68 mg; $^1$H NMR (400 MHz, Deuterium Oxide) δ 8.63-6.72 (m, 4H), 4.57-2.78 (m, 20H), 2.75-1.47 (m, 4H).

Synthesis of Compound 21 (Polymer Molecular Weight=22k, Heterocycle Grafting=21%)

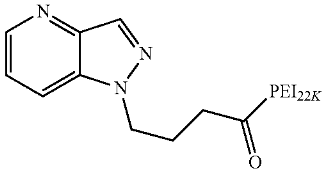

Compound 21 was prepared analogously to the general procedure, step 3 (Example 1). Yield=97%; m=73 mg; $^1$H NMR (400 MHz, Deuterium Oxide) δ 9.12-7.56 (m, 4H), 4.58-4.36 (m, 2H), 4.09-3.01 (m, 19H), 2.90-1.77 (m, 4H).

Synthesis of Compound 22 (Polymer Molecular Weight=22k, Heterocycle Grafting=21%)

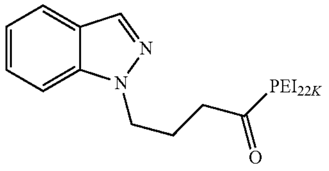

Compound 22 was prepared analogously to the general procedure, step 3 (Example 1). Yield=52%; m=39 mg; $^1$H NMR (400 MHz, Deuterium Oxide) δ 8.21-6.38 (m, 5H), 4.47-1.37 (m, 25H).

Synthesis of Compound 23 (Polymer Molecular Weight=22k, Heterocycle Grafting=26%)

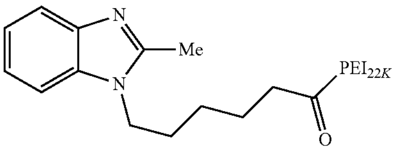

Compound 23 was prepared analogously to the general procedure, step 3 (Example 1). Yield=97%; m=169 mg; $^1$H NMR (400 MHz, Deuterium Oxide) δ 7.74-7.19 (m, 4H), 4.41-3.00 (m, 13H), 2.83-2.52 (m, 3H), 2.48-1.99 (m, 2H), 1.95-1.00 (m, 6H).

Synthesis of Compound 24 (Polymer Molecular Weight=8k, Heterocycle Grafting=20%)

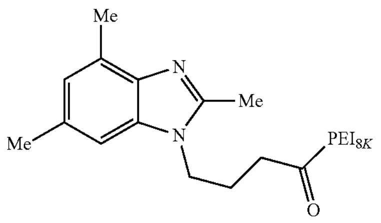

Compound 24 was prepared analogously to the general procedure, step 3 (Example 1). Yield=70%; m=22 mg; $^1$H NMR (400 MHz, Deuterium Oxide) δ 7.80-6.15 (m, 2H), 4.50-3.21 (m, 22H), 3.17-0.97 (m, 13H).

Synthesis of Compound 25 (Polymer Molecular Weight=10k, Heterocycle Grafting=20%)

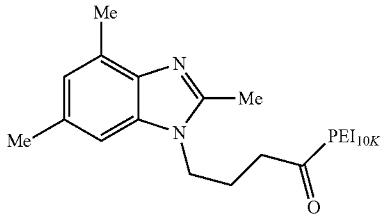

Compound 25 was prepared analogously to the general procedure, step 3 (Example 1). Yield=73%; m=23 mg; $^1$H NMR (400 MHz, Deuterium Oxide) δ 7.98-6.15 (m, 2H), 4.62-3.06 (m, 22H), 2.99-1.39 (m, 13H).

Synthesis of Compound 26 (Polymer Molecular Weight=15k, Heterocycle Grafting=17%)

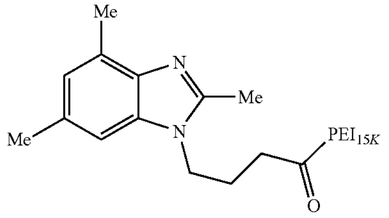

Compound 26 was prepared analogously to the general procedure, step 3 (Example 1). Yield=84%; m=25 mg; $^1$H NMR (400 MHz, Deuterium Oxide) δ 7.64-6.35 (m, 2H), 4.57-3.13 (m, 25H), 3.13-1.50 (m, 13H).

Synthesis of Compound 27 (Polymer Molecular Weight=30k, Heterocycle Grafting=18%)

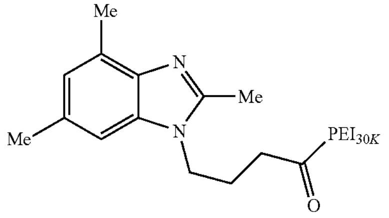

Compound 27 was prepared analogously to the general procedure, step 3 (Example 1). Yield=68%; m=21 mg; $^1$H NMR (400 MHz, Deuterium Oxide) δ 7.74-6.35 (m, 2H), 4.50-3.01 (m, 24H), 2.97-1.41 (m, 13H).

Synthesis of Compound 28 (Polymer Molecular Weight=25k, Heterocycle Grafting=22%)

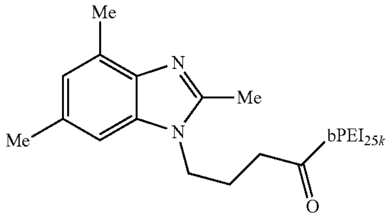

Compound 28 was prepared analogously to the general procedure, step 3 using branched polyethyleneimine (bPEI, 25K, Sigma-Aldrich). Yield=94%; m=282 mg; $^1$H NMR (400 MHz, Deuterium Oxide) δ 7.42-6.52 (m, 2H), 4.45-1.51 (m, 33H).

Synthesis of Compound 29 (Polymer Molecular Weight=10k, Heterocycle Grafting=29%)

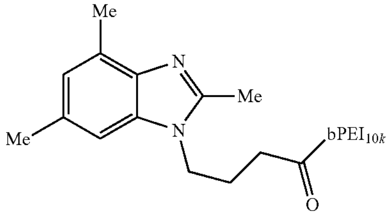

Compound 29 was prepared analogously to the general procedure, step 3 using branched polyethyleneimine (bPEI, 10K, Alfa Aesar). Yield=99%; m=351 mg; $^1$H NMR (400 MHz, Deuterium Oxide) δ 7.37-6.50 (m, 2H), 4.57-1.44 (m, 29H).

Synthesis of Compound 30 (Polymer Molecular Weight=22k, Heterocycle Grafting=35%)

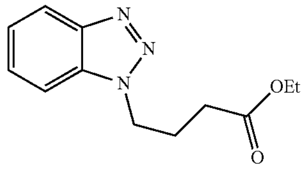 [SMILES: CCOC(=O)CCCn1nnc2ccccc21]

Intermediate 30a was prepared analogously to the general procedure, step 1 (Example 1). Yield=17%; m=1.00 g; $^1$H NMR (400 MHz, Chloroform-d) δ 7.95 (d, J=8.4 Hz, 1H), 7.45 (d, J=8.3 Hz, 1H), 7.38 (t, J=7.6 Hz, 1H), 7.30-7.22 (m, 1H), 4.68-4.57 (m, 2H), 4.01 (qd, J=7.1, 1.6 Hz, 2H), 2.30-2.16 (m, 4H), 1.13 (td, J=7.1, 1.6 Hz, 3H).

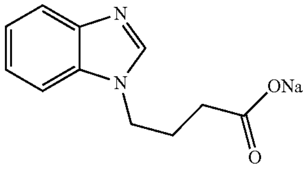

Intermediate 30b was prepared analogously to the general procedure, step 2 (Example 1). Yield=85%; m=830 mg; $^1$H NMR (400 MHz, Methanol-$d_4$) δ 8.03-7.96 (m, 1H), 7.82 (d, J=8.5 Hz, 1H), 7.58 (t, J=7.3 Hz, 1H), 7.45 (t, J=8.0 Hz, 1H), 4.80 (dt, J=7.0, 4.3 Hz, 2H), 2.37 (t, J=7.0 Hz, 2H), 2.30 (q, J=7.0 Hz, 2H).

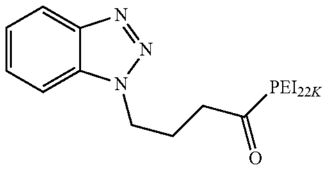

Compound 30 was prepared analogously to the general procedure, step 3 (Example 1). Yield=100%; m=189 mg; $^1$H NMR (400 MHz, Deuterium Oxide) δ 7.41-6.55 (m, 4H), 4.58-3.02 (m, 14H), 2.90-1.31 (m, 3H).

Synthesis of Compound 31 (Polymer Molecular Weight=22k, Heterocycle Grafting=35%)

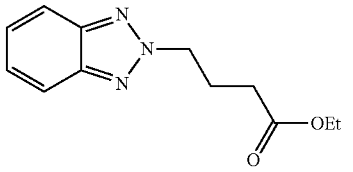 [SMILES: CCOC(=O)CCCn1nc2ccccc2n1]

Intermediate 31a was prepared analogously to the general procedure, step 1 (Example 1). Yield=34%; m=2.00 g; $^{1}H$ NMR (400 MHz, Chloroform-d) δ 7.73 (ddt, J=7.4, 4.1, 2.2 Hz, 2H), 7.25 (ddt, J=9.4, 4.0, 2.2 Hz, 2H), 4.68 (dd, J=7.3, 5.5 Hz, 2H), 3.99 (ddd, J=9.1, 7.2, 6.0 Hz, 2H), 2.40-2.12 (m, 4H), 1.11 (tt, J=7.3, 1.3 Hz, 3H).

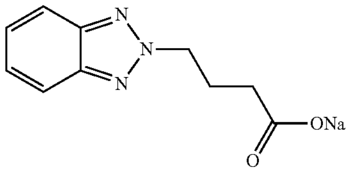

Intermediate 31b was prepared analogously to the general procedure, step 2 (Example 1). Yield=53%; m=1.00 g; $^{1}H$ NMR (400 MHz, Methanol-$d_4$) δ 7.86 (dd, J=6.9, 3.4 Hz, 2H), 7.42 (dd, J=6.9, 3.4 Hz, 2H), 4.83 (d, J=13.0 Hz, 2H), 2.37 (d, J=4.3 Hz, 4H).

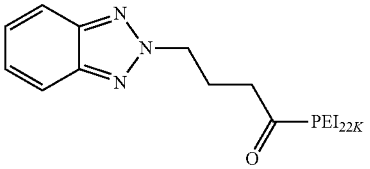

Compound 31 was prepared analogously to the general procedure, step 3 (Example 1). Yield=100%; m=166 mg; $^{1}H$ NMR (400 MHz, Deuterium Oxide) δ 7.83-6.50 (m, 4H), 4.61-3.90 (m, 2H), 3.88-2.51 (m, 11H), 2.49-1.35 (m, 4H).

Synthesis of Compound 32 (Polymer Molecular Weight=22k, Heterocycle Grafting=22%)

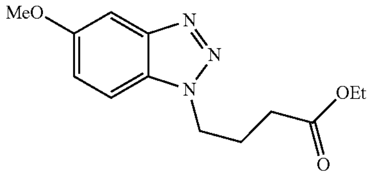 [SMILES: CCOC(=O)CCCn1nnc2cc(OC)ccc21]

Intermediate 32a was prepared analogously to the general procedure, step 1 (Example 1). Yield=23%; m=1.69 g; $^{1}H$ NMR (400 MHz, Chloroform-d) δ 7.78 (dd, J=9.1, 1.9 Hz, 1H), 7.34 (dd, J=9.1, 1.9 Hz, 0H), 7.26 (d, J=2.3 Hz, 0H), 7.05 (dd, J=9.0, 2.2 Hz, 0H), 6.89 (dd, J=9.1, 2.2 Hz, 1H), 6.73 (d, J=2.2 Hz, 1H), 4.55 (dtd, J=13.6, 6.7, 1.9 Hz, 2H), 4.01 (q, J=7.1 Hz, 2H), 3.78 (dd, J=6.6, 1.8 Hz, 3H), 3.04 (s, 0H), 2.22 (ddd, J=19.8, 7.7, 4.2 Hz, 4H), 1.13 (td, J=7.1, 1.8 Hz, 3H).

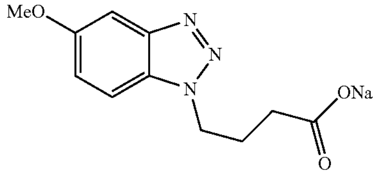

Intermediate 32b was prepared analogously to the general procedure, step 2 (Example 1). Yield=70%; m=1.16 g; $^{1}H$ NMR (400 MHz, Methanol-$d_4$) δ 7.81 (dd, J=9.1, 2.7 Hz, 1H), 7.67 (dd, J=8.9, 2.7 Hz, 0H), 7.33 (s, 0H), 7.24-7.15 (m, 1H), 7.05 (dd, J=9.1, 2.7 Hz, 1H), 4.73 (qd, J=7.1, 2.3 Hz, 2H), 3.91 (dd, J=13.2, 2.8 Hz, 3H), 3.33 (d, J=3.2 Hz, 0H), 2.35 (t, J=6.7 Hz, 2H), 2.26 (t, J=7.3 Hz, 2H).

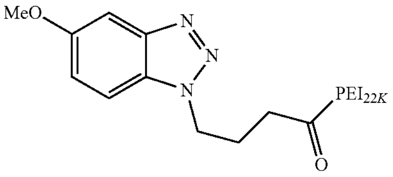

Compound 32 was prepared analogously to the general procedure, step 3 (Example 1). Yield=96%; m=153 mg; $^{1}H$ NMR (400 MHz, Deuterium Oxide) δ 7.99-6.22 (m, 3H), 4.49-4.03 (m, 2H), 3.96-2.80 (m, 21H), 2.63-1.55 (m, 4H).

Synthesis of Compound 33 (Polymer Molecular Weight=22k, Heterocycle Grafting=18%)

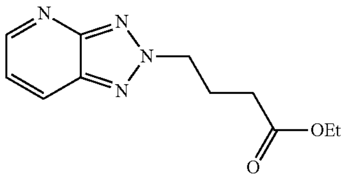 [SMILES: CCOC(=O)CCCn1nc2cccnc2n1]

Intermediate 33a was prepared analogously to the general procedure, step 1 (Example 1). Yield=18%; m=254 mg; $^{1}H$ NMR (400 MHz, Chloroform-d) δ 8.53 (dd, J=4.4, 1.5 Hz, 1H), 7.82 (dd, J=8.4, 1.5 Hz, 1H), 7.24 (dd, J=8.4, 4.4 Hz, 1H), 4.54 (t, J=6.8 Hz, 2H), 3.89 (q, J=7.1 Hz, 2H), 2.20-2.05 (m, 4H), 1.01 (t, J=7.1 Hz, 3H).

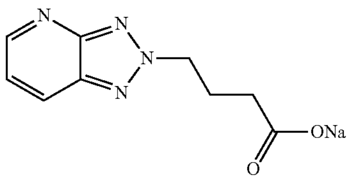

Intermediate 33b was prepared analogously to the general procedure, step 2 (Example 1). Yield=98%; m=242 mg; $^{1}H$ NMR (400 MHz, Deuterium Oxide) δ 8.59 (dq, J=4.5, 1.5 Hz, 1H), 8.21 (dt, J=8.5, 1.6 Hz, 1H), 7.52 (ddt, J=8.5, 4.5, 1.4 Hz, 1H), 4.70-4.62 (m, 2H), 2.21-2.04 (m, 4H).

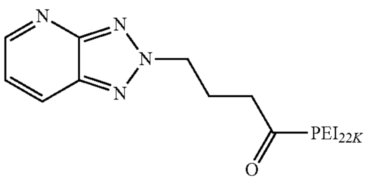

Compound 33 was prepared analogously to the general procedure, step 3 (Example 1). Yield=75%; m=54 mg; $^1$H NMR (400 MHz, Deuterium Oxide) δ 9.06-6.76 (m, 3H), 4.16-2.96 (m, 20H), 2.93-1.52 (m, 4H).

Synthesis of Compound 34 (Polymer Molecular Weight=22k, Heterocycle Grafting=17%)

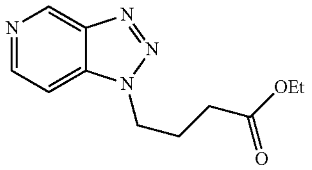 [SMILES: CCOC(=O)CCCn1nnc2cnccc21]

Intermediate 34a was prepared analogously to the general procedure, step 1 (Example 1). Yield=52%; m=600 mg; $^1$H NMR (400 MHz, Chloroform-d) δ 9.51-9.16 (m, 1H), 8.60-8.50 (m, 1H), 7.96-7.52 (m, 1H), 4.90-4.71 (m, 2H), 4.10 (dq, J=8.6, 7.1 Hz, 2H), 2.43-2.30 (m, 4H), 1.23 (t, J=7.2 Hz, 3H).

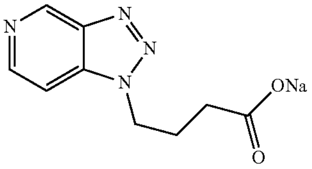

Intermediate 34b was prepared analogously to the general procedure, step 2 (Example 1). Yield=97%; m=550 mg; $^1$H NMR (400 MHz, Deuterium Oxide) δ 9.27-9.11 (m, 1H), 8.43-8.27 (m, 1H), 7.95-7.69 (m, 1H), 4.84-4.63 (m, 2H), 2.28-2.05 (m, 4H).

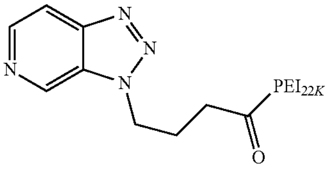

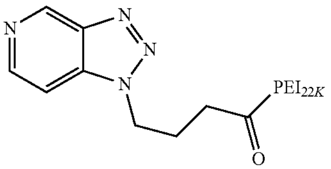

Compound 34 was prepared analogously to the general procedure, step 3 (Example 1). Yield=95%; m=68 mg; $^1$H NMR (400 MHz, Deuterium Oxide) δ 10.08-8.17 (m, 3H), 4.21-2.84 (m, 25H), 2.83-1.64 (m, 4H).

Example 3. Thermal Inactivation of Viral Vectors

Heat inactivation of viral vectors is often performed around 70° C. in the presence of 0.05-0.1% SDS (Sommer J M, et al. *Molecular therapy: the journal of the American Society of Gene Therapy* 2003, 7(1), 122-128; Gargi Maheshwari, et al. *Journal of Virological Methods* 2004, 118(2) 141-146; Fabian Kriesel et al. *Journal of Virological Methods* 2020, 276, 113768). It usually takes one hour to perform these inactivation protocols. However, to avoid the addition of chemical and to reduce heating time, the inventors studied the thermal inaction at 120° C. for 30 minutes.

Figure 3:
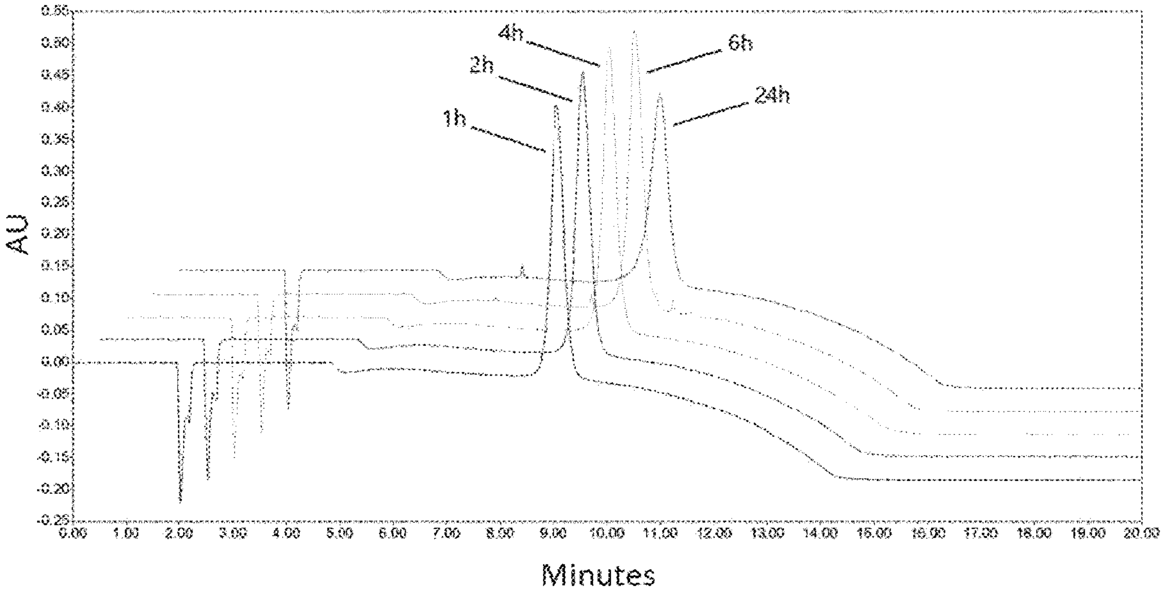
FIG. 3. Optimization of thermal inactivation with compound 05.

Therefore, the stability of compound 05 at 120° C. over 24 hours was evaluated. An overlay of the different chromatograms at different timepoints s represented in FIG. 3. No degradation was observed over 4 hours. After 6 hours, peaks were detected around compound 05 of interest meaning slight degradation. Based on this stability study, the possible residual reagent in the sample is not affected by the autoclave treatment during 30 minutes.

Example 4. Optimization of Acidic Hydrolysis

The inventors studied 3 different parameters to define the best conditions where compound 05 will not be degraded:

Type of acids,

Temperature,

Heating time.

Acidic hydrolysis with 20 ppm of compound 05 was performed with HCl, $H_2SO_4$, $HNO_3$, which are 3 acids known to degrade proteins or nucleic acid.

To a solution of compound 05 (20 ppm) in distillated water was added respectively chlorhydric, sulfuric or nitric acid. The 3 mixtures were heated at 100° C. overnight. For each acid, the following methodology was followed:

Accuracy on reference substance compound 05 in triplicate. This test consists in hydrolyzing the reference substance at 20 ppm with the different acid and perform the treatment on a centrifugal filter. The acidic hydrolysis with HCl was performed over 46 hours (15 hours for the other acids).

Recovery on the virus spiked at 20 ppm with compound 05. This parameter was determined on 3 injections.

The different results are summarized in Table 3 and demonstrate that any condition is able to avoid degradation of compound 05. However, chlorhydric acid demonstrates the best reproducibility compared to sulfuric or nitric acids.

TABLE 3

| Recovery results with different acids used for the acidic hydrolysis. | | | | | |
|---|---|---|---|---|---|
| | Virus spiked at 20 ppm with compound 05 | | | | |
| Acid type | Recovery - Injection 1 | Recovery - Injection 2 | Recovery - Injection 3 | Average | Standard deviation |
| HCl - after 15 hours | 49.5 | 40.0 | 54.0 | 47.8 | 15.0 |
| HCl - after 46 hours | 18.8 | 18.8 | 20.0 | 19.2 | 3.5 |
| $H_2SO_4$ | 42.1 | 79.9 | 75.6 | 65.8 | 31.4 |
| $HNO_3$ | 3.5 | 6.6 | 34.4 | 14.8 | 115 |

Concentration of HCl and heating time are critical for the acidic hydrolysis. Thus the inventors evaluated these 2 criteria:

Concentration of HCl: 10%, 1%, 0.1%,

Heating time at 60° C., 80° C., 100° C.: t0, +1 h, +2 h, +3 h, +4 h, +5 h, +6, +24 h.

Finally, the optimized conditions were fixed to an acidic hydrolysis in a chlorhydric solution 0.1% at 100° C. for 2 hours. Linearity in FIG. 4*a*, FIG. 4*b* and FIG. 5 shows a LOD=1.97 and LOQ=6.55.

Figure 4A:
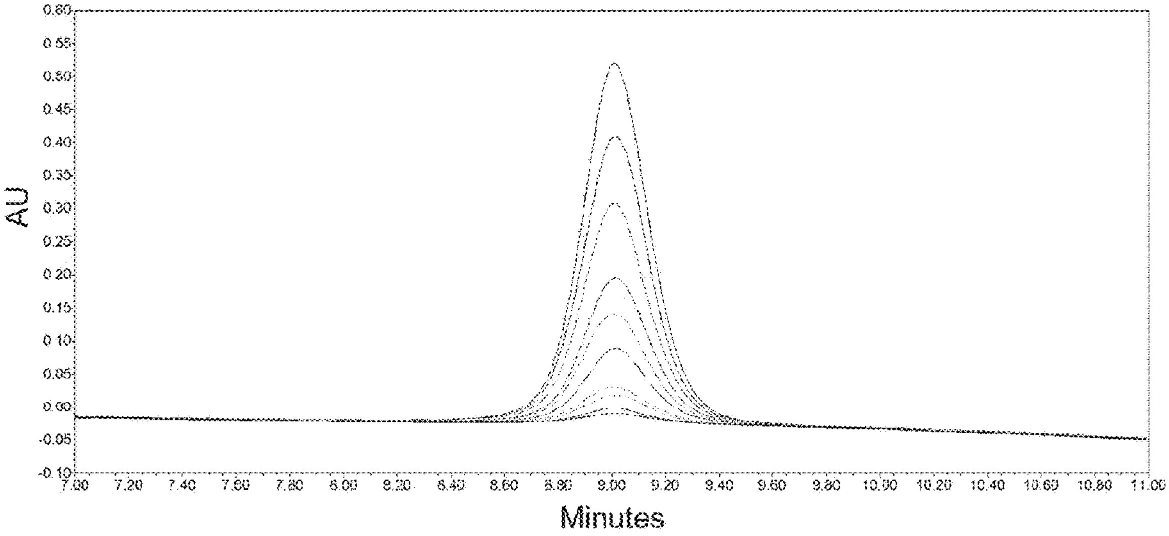
FIG. 4*a*. Hydrolysis of compound 05. Figure FIG.. 4*b*. Overlay of FIG. 4*a*.
Figure 4B:
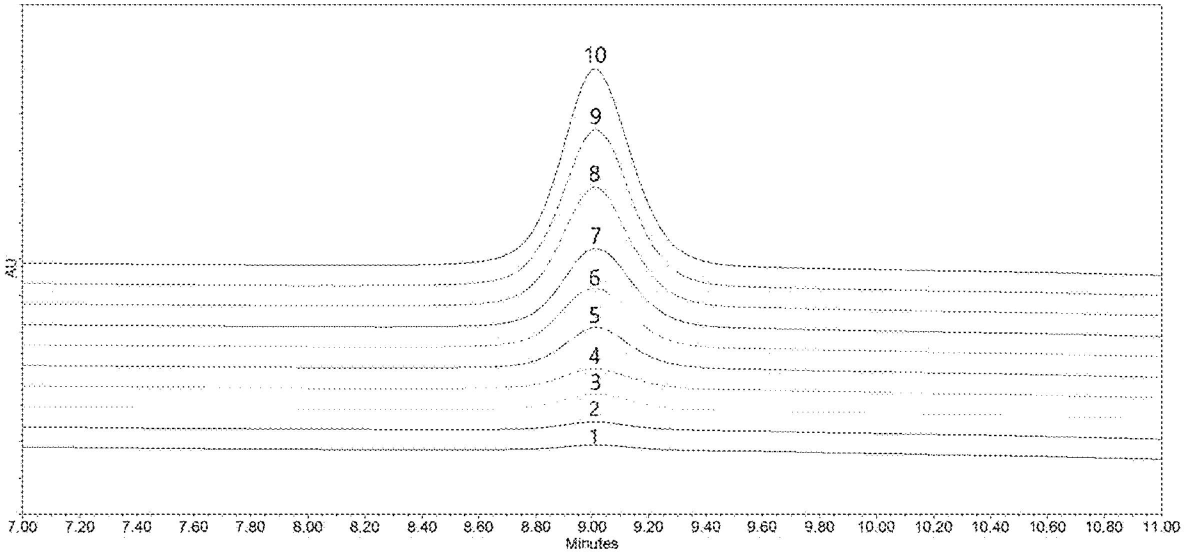
FIG. 4.
Figure 5:
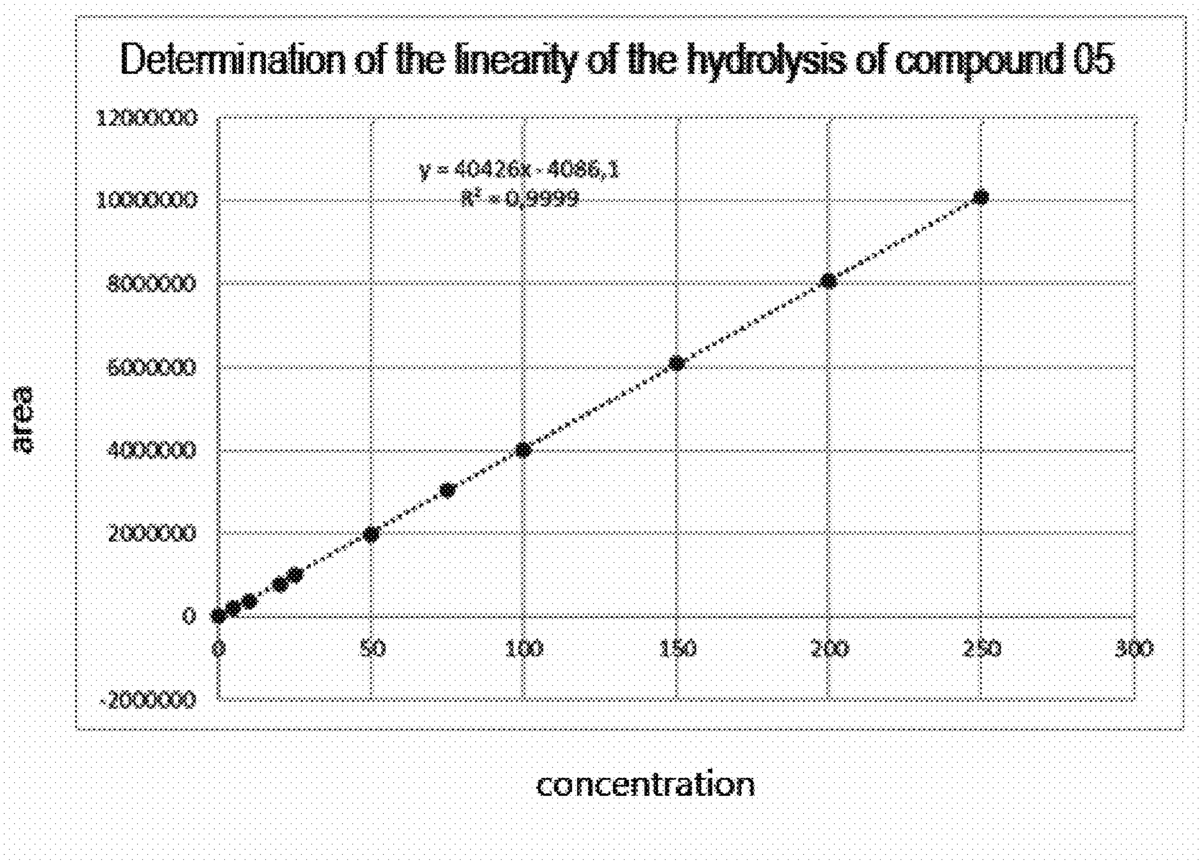
FIG. 5. Determination of the linearity of the hydrolysis of compound 05.

FIG. 4*b* shows an overlay of the FIG. 4*a*. 1 represents the compound 5, 5ppm at 110° C.; 2 represents the compound 5, 10 ppm at 110° C.; 3 represents the compound 5, 20 ppm at 110° C.; 4 represnets the compound 5, 25 ppm at 110° C.; 5 represents the compound 5, 50 ppm at 110° C.; 6 represents the compound 6, 75 ppm at 110° C.; 7 represents the compound 5, 100 ppm at 110° C.; 8 represents the compound 5, 150 ppm at 110° C.

Example 5. Qualitative and Quantitative Analysis of the Residual Product

The HPLC method is described in Table 4 below. This analytical method was developed during the whole development of the invention because of two main issues:

Presence of carry-over which could impact the quantification,

The symmetry of the different peaks which was not optimal considering a potential validation of the method.

Different "in-house" tests were performed by the inventors in order to tackle the carry-over issue by varying different parameters such as the column type (grafted $C_4$ vs $C_{18}$, AX vs Peptide), the mobile phases composition, gradient slope and flow rate. After those different screenings, a new analytical method was put in place and is described in Table 4 below.

TABLE 4

| Description of the analytical method used during the development of the residual test. | | | | | |
|---|---|---|---|---|---|
| | Method | | | | |
| Column | Waters Xbridge ® Peptide BEH C4Column, 300 Å, 3.5 μm particle size | | | | |
| Column size | 4.6 mm × 150 mm | | | | |
| Flow rate | 1.0 mL/min | | | | |
| Injection Volume | 100 μL | | | | |
| Detection | UV | | | | |
| Wavelength | 235 nm | | | | |
| UV sampling rate | 20 pts/sec | | | | |
| Column temperature | 25 ± 2° C. | | | | |
| Autosampler temperature | Room temperature | | | | |
| Run time | 40.0 min | | | | |
| Mobile phase A | TFA at 1% in water | | | | |
| Mobile phase B | Acetonitrile | | | | |
| | Time (min) | Flow (mL/min) | % A | % B | Curve |
| Gradient | 0 | 1.0 | 95.00 | 5.00 | 6 |
| | 2.5 | 1.0 | 95.00 | 5.00 | 6 |
| | 12.0 | 1.0 | 10.00 | 90.00 | 6 |
| | 35.0 | 1.0 | 10.00 | 90.00 | 6 |
| | 35.1 | 1.0 | 95.00 | 5.00 | 6 |
| | 40 | 1.0 | 95.00 | 5.00 | 6 |
| Wash solvent composition | 1% TFA in Water/Acetonitrile 75/25(v/v) | | | | |
| Purge solvent composition | 0.1% TFA in Water/Acetonitrile 90/10 (v/v) | | | | |
| Pre-injection wash time | 15 sec | | | | |
| Post-injection wash time | 30 sec | | | | |

Example 6. Experimental Section

The inventors demonstrated the method efficiency on a variety of transfection reagents (for example as described in WO2021/023796; WO2021/023798) which showed strong activity in transfection, in particular for viral vector's production.

The inventors studied the stability of all the transfection reagentscompounds 01 to 34 under the acidic hydrolysis described previously (Table 5). Most of the molecules were fully stable under the acidic conditions. Moreover, based on the study of both limit of detection (LOD) and limit of quantification (LOQ), the analytical method was applicable to a large variety of PEI-based polymers.

TABLE 5
Examples of polymers used in the present invention (n.d. = not detected, experiments: A transfection reagent (20 ppm) in a solution of HCl (2 mL, 0.1%) was heated at 110° C. for 2 hours. After cooling, the experiment was directly analyzed by HPLC.)
| Compounds | Structures | Polymer | Grafting (%) | LOD (ppm) | LOQ (ppm) | Degree of hydrolysis (%) |
|---|---|---|---|---|---|---|
| 01 | 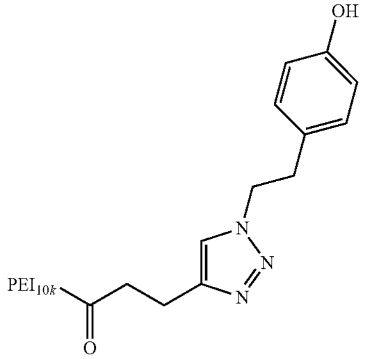 | IPEI$_{10k}$ | 16 | 7.4 | 24.68 | n.d. |
| 02 | 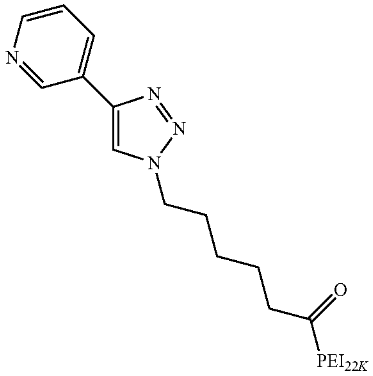 | IPEI$_{22k}$ | 18 | 0.73 | 2.42 | n.d. |
| 03 | 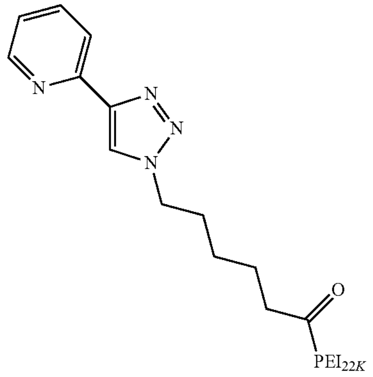 | IPEI$_{22k}$ | 18 | 0.76 | 2.52 | n.d. |
| 04 | 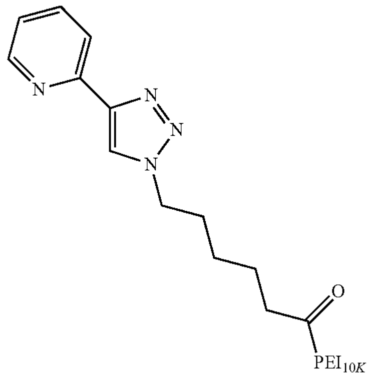 | IPEI$_{10k}$ | 22 | 0.42 | 1.40 | n.d |

TABLE 5-continued

Examples of polymers used in the present invention (n.d. = not detected, experiments: A transfection reagent (20 ppm) in a solution of HCl (2 mL, 0.1%) was heated at 110° C. for 2 hours. After cooling, the experiment was directly analyzed by HPLC.)

| Compounds | Structures | Polymer | Grafting (%) | LOD (ppm) | LOQ (ppm) | Degree of hydrolysis (%) |
|---|---|---|---|---|---|---|
| 05 | 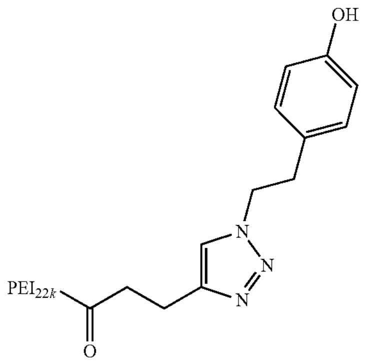 | $IPEI_{22k}$ | 22 | 2.52 | 8.41 | n.d. |
| 06 | 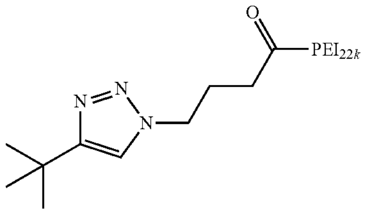 | $IPEI_{22k}$ | 16 | 3.18 | 10.61 | n.d. |
| 07 | 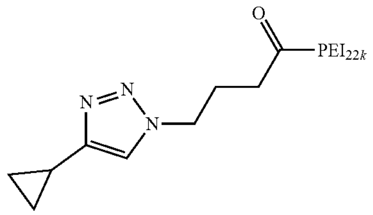 | $IPEI_{22k}$ | 19 | 0.94 | 3.14 | n.d. |
| 08 | 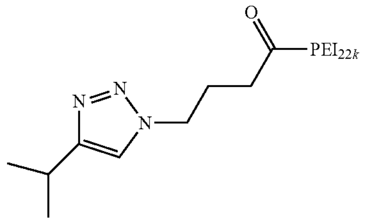 | $IPEI_{22k}$ | 19 | 3.91 | 13.02 | n.d. |
| 09 | 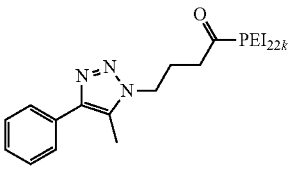 + 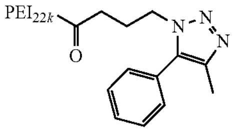 | $IPEI_{22k}$ | 22 | 3.49 | 11.62 | n.d. |
| 10 | 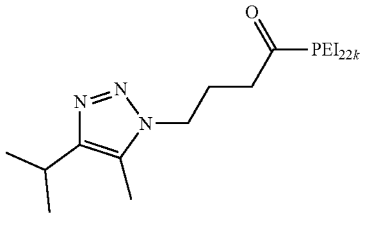 | $IPEI_{22k}$ | 21 | 2.14 | 7.14 | n.d. |

TABLE 5-continued

Examples of polymers used in the present invention (n.d. = not detected, experiments: A transfection reagent (20 ppm) in a solution of HCl (2 mL, 0.1%) was heated at 110° C. for 2 hours. After cooling, the experiment was directly analyzed by HPLC.)

| Compounds | Structures | Polymer | Grafting (%) | LOD (ppm) | LOQ (ppm) | Degree of hydrolysis (%) |
|---|---|---|---|---|---|---|
| 11 | 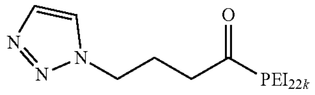 | $IPEI_{22k}$ | 25 | 2.96 | 9.86 | n.d. |
| 12 | 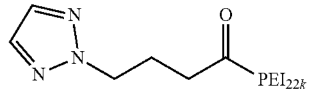 | $IPEI_{22k}$ | 25 | 0.51 | 1.69 | n.d. |
| 13 | 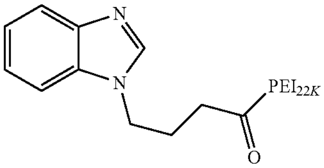 | $IPEI_{22k}$ | 10 | 0.73 | 2.42 | n.d. |
| 14 | 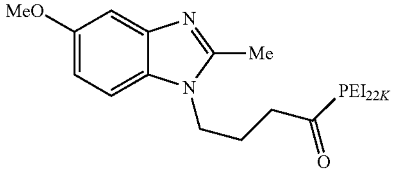 | $IPEI_{22k}$ | 24 | 0.65 | 2.16 | n.d. |
| 15 | 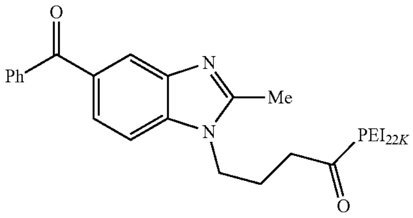 | $IPEI_{22k}$ | 27 | 1.92 | 6.39 | n.d. |
| 16 | 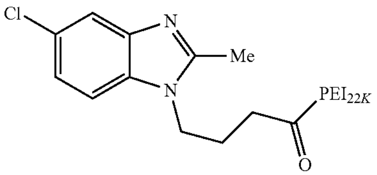 | $IPEI_{22k}$ | 30 | 1.49 | 4.97 | n.d. |
| 17 | 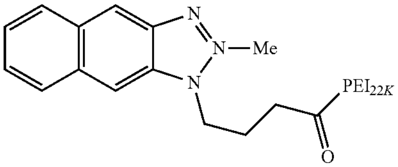 | $IPEI_{22k}$ | 26 | 0.17 | 0.58 | n.d. |
| 18 | 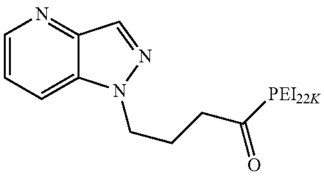 | $IPEI_{22k}$ | 47 | 0.42 | 1.39 | n.d. |

TABLE 5-continued

Examples of polymers used in the present invention (n.d. = not detected, experiments: A transfection reagent (20 ppm) in a solution of HCl (2 mL, 0.1%) was heated at 110° C. for 2 hours. After cooling, the experiment was directly analyzed by HPLC.)

| Compounds | Structures | Polymer | Grafting (%) | LOD (ppm) | LOQ (ppm) | Degree of hydrolysis (%) |
|---|---|---|---|---|---|---|
| 19 | 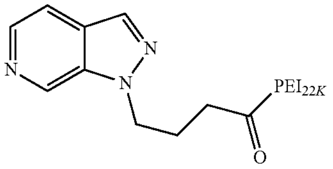 | $IPEI_{22k}$ | 25 | 0.24 | 0.81 | n.d. |
| 20 | 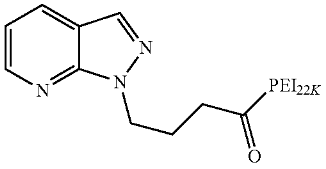 | $IPEI_{22k}$ | 22 | 0.94 | 3.12 | n.d. |
| 21 | 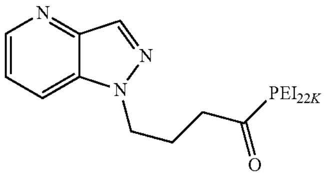 | $IPEI_{22k}$ | 21 | 0.26 | 0.85 | n.d. |
| 22 | 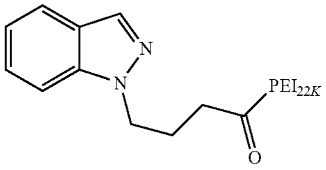 | $IPEI_{22k}$ | 21 | 5.83 | 19.45 | n.d. |
| 23 | 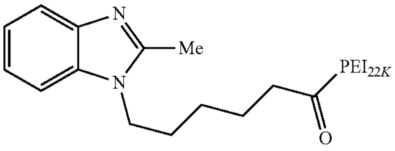 | $IPEI_{22k}$ | 26 | 0.31 | 1.04 | n.d. |
| 24 | 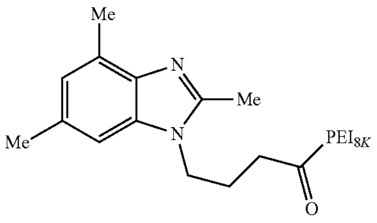 | $IPEI_{22k}$ | 11 | 2.93 | 9.76 | n.d. |
| 25 | 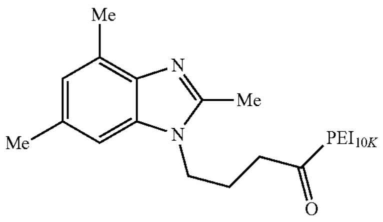 | $IPEI_{10k}$ | 20 | 1.90 | 6.33 | n.d. |

TABLE 5-continued

Examples of polymers used in the present invention (n.d. = not detected, experiments: A transfection reagent (20 ppm) in a solution of HCl (2 mL, 0.1%) was heated at 110° C. for 2 hours. After cooling, the experiment was directly analyzed by HPLC.)

| Compounds | Structures | Polymer | Grafting (%) | LOD (ppm) | LOQ (ppm) | Degree of hydrolysis (%) |
|---|---|---|---|---|---|---|
| 26 | 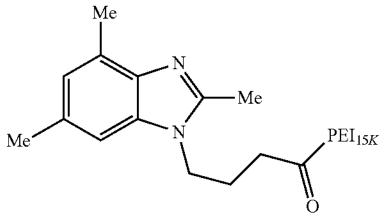 | IPEI$_{15k}$ | 17 | 2.53 | 8.43 | n.d. |
| 27 | 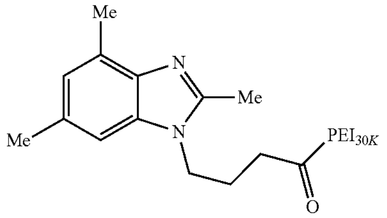 | IPEI$_{30k}$ | 18 | 1.87 | 6.23 | n.d. |
| 28 | 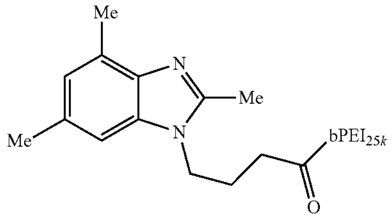 | bPEI$_{25k}$ | 22 | 9.32 | 31.07 | 4 |
| 29 | 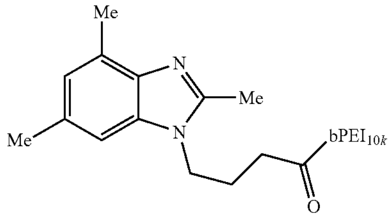 | bPEI$_{10k}$ | 29 | 8.78 | 29.25 | 9 |
| 30 | 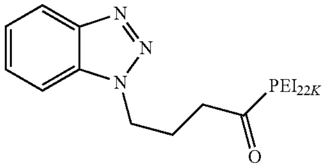 | IPEI$_{22k}$ | 35 | 4.11 | 13.7 | n.d. |
| 31 | 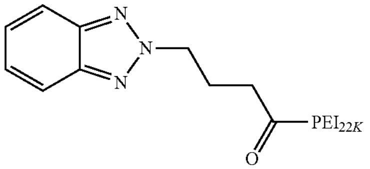 | IPEI$_{22k}$ | 35 | 7.72 | 25.72 | n.d. |
| 32 | 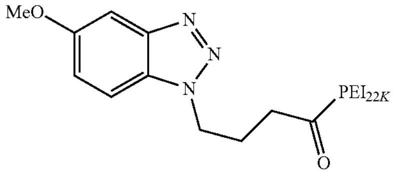 | IPEI$_{22k}$ | 22 | 10.58 | 35.26 | n.d. |

TABLE 5-continued

Examples of polymers used in the present invention (n.d. = not detected, experiments: A transfection reagent (20 ppm) in a solution of HCl (2 mL, 0.1%) was heated at 110° C. for 2 hours. After cooling, the experiment was directly analyzed by HPLC.)

| Compounds | Structures | Polymer | Grafting (%) | LOD (ppm) | LOQ (ppm) | Degree of hydrolysis (%) |
|---|---|---|---|---|---|---|
| 33 | 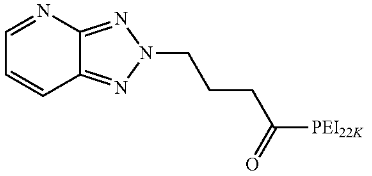 | $IPEI_{22k}$ | 18 | 0.8 | 2.67 | 23 |
| 34 | 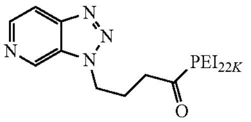 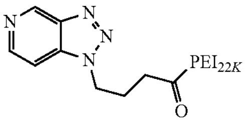 | $IPEI_{22k}$ | 17 | 0.84 | 2.79 | n.d. |

Then the inventors applied the whole residual test described above on a selection of molecules listed in Table 6 below.

TABLE 6

Residual test. n.d. = not detected; Procedure for spike (adding a known quantity of transfection agent; Araujo, Journal of Chromatography B, 2009, 877(23), 2224-2234) before hydrolysis: to a solution of viral vector (AAV, 200 μL) was added a solution of HCl (0.37%, 108 μL), a volume of pure water (92 μL) and a solution of transfection reagent (conc: 100 ppm, 80 μL).

| Compounds | Structures | LOD (ppm) | LOQ (ppm) | Recovery (%) | Degree of hydrolysis |
|---|---|---|---|---|---|
| 27 | 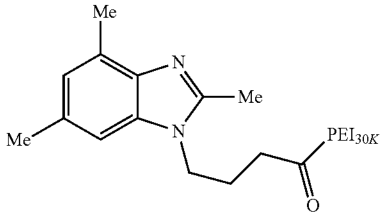 | 1.87 | 6.23 | Spike before hydrolysis: 73 Spike after hydrolysis: 80 | n.d. |
| 04 | 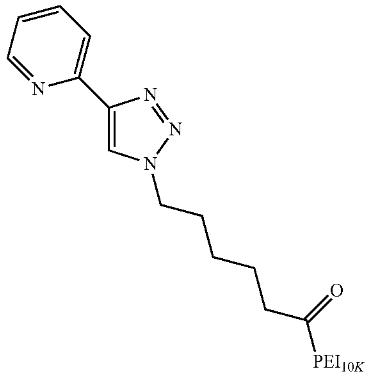 | 0.42 | 1.40 | Spike before hydrolysis: 89 Spike after hydrolysis: 89 | n.d. |
| 07 | 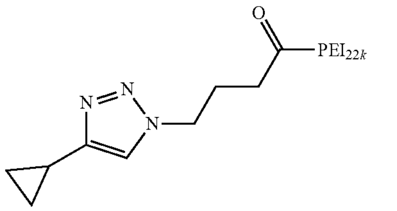 | 0.94 | 3.14 | Spike before hydrolysis: 59 Spike after hydrolysis: 93 | n.d. |

TABLE 6-continued

Residual test. n.d. = not detected; Procedure for spike (adding a known quantity of transfection agent; Araujo, Journal of Chromatography B, 2009, 877(23), 2224-2234) before hydrolysis: to a solution of viral vector (AAV, 200 μL) was added a solution of HCl (0.37%, 108 μL), a volume of pure water (92 μL) and a solution of transfection reagent (conc: 100 ppm, 80 μL).

| Compounds | Structures | LOD (ppm) | LOQ (ppm) | Recovery (%) | Degree of hydrolysis |
|---|---|---|---|---|---|
| 10 | 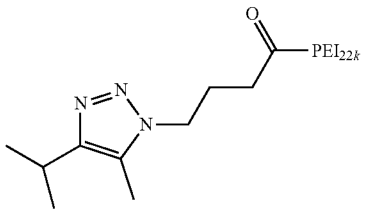 | 2.14 | 7.14 | Spike before hydrolysis: 78 Spike after hydrolysis: 85 | n.d. |
| 14 | 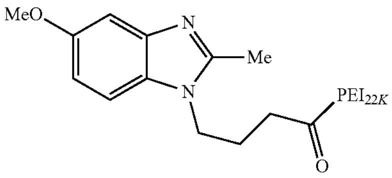 | 0.65 | 2.16 | Spike before hydrolysis: 89 Spike after hydrolysis: 82 | n.d. |
| 17 | 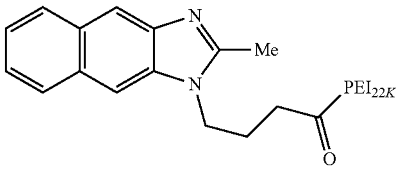 | 0.17 | 0.58 | Spike before hydrolysis: 72 Spike after hydrolysis: 89 | n.d. |
| 26 | 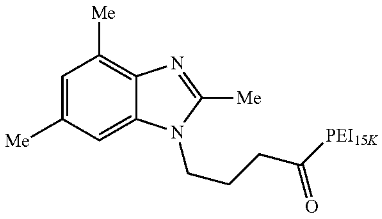 | 2.56 | 8.43 | Spike before hydrolysis: 82 Spike after hydrolysis: 85 | n.d. |
| 22 | 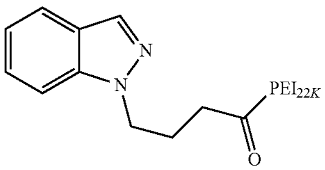 | 5.83 | 19.45 | Spike before hydrolysis: 75 Spike after hydrolysis: 82 | n.d. |
| 19 | 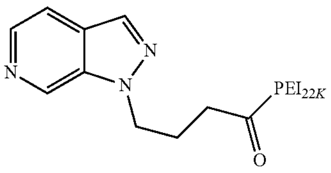 | 0.24 | 0.81 | Spike before hydrolysis: 73 Spike after hydrolysis: 76 | n.d. |

TABLE 6-continued

Residual test. n.d. = not detected; Procedure for spike (adding a known quantity of transfection agent; Araujo, Journal of Chromatography B, 2009, 877(23), 2224-2234) before hydrolysis: to a solution of viral vector (AAV, 200 μL) was added a solution of HCl (0.37%, 108 μL), a volume of pure water (92 μL) and a solution of transfection reagent (conc: 100 ppm, 80 μL).

| Compounds | Structures | LOD (ppm) | LOQ (ppm) | Recovery (%) | Degree of hydrolysis |
|---|---|---|---|---|---|
| 05 | 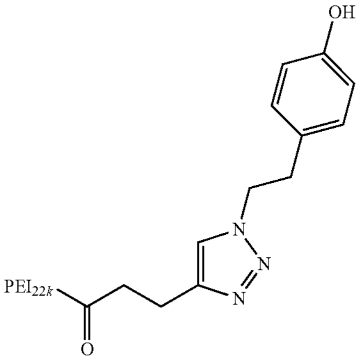 | 2.52 | 8.41 | Spike before hydrolysis: 84 Spike after hydrolysis: 68 | n.d. |

The tube was sealed then heated at 100° C. for 2 hours. After cooling to room temperature, the mixture was diluted in 3.5 mL pure water then filtered by centrifugation using a centrifugal filter with a minimal cut-off ok 1 kDa for 30 minutes at 5.000 g to afford a solution between 250-300 μL. The solution was completed to 4 mL and filtered at 5.000 g for 60 minutes. The same procedure was repeated 2 more times. The final retentate was diluted with pure water to give a solution of 500 μL and analyzed by HPLC.

Procedure for spike after hydrolysis: to a solution of viral vector (AAV, 200 μL) was added a solution of HCl (0.37%, 108 μL), a volume of pure water (92 μL) and a solution of transfection reagent (conc: 100 ppm, 80 μL). The tube was sealed then heated at 100° C. for 2 hours. After cooling, a solution of transfection reagent (conc: 100 ppm, 80 μL) was added before the filtration process.

Examples of buffers used with compound 17 are disclosed in Table 7.

TABLE 7

Examples of buffer with compound 17.

| buffer | Recovery (%) | Degree of hydrolysis |
|---|---|---|
| HEPES | Spike before hydrolysis: 26 Spike after hydrolysis: 51 | n.d. |
| D-PBS ($Na_2HPO_4$ 10 mM + $KH_2PO_4$ 1.8 mM pH = 7.4 + KCl 27 mM + NaCl 137 mM) | Spike before hydrolysis: 66 Spike after hydrolysis: 84 | n.d. |
| NaCl (150 mM) | Spike before hydrolysis: 76 Spike after hydrolysis: 86 | n.d. |
| Sodium citrate (0.1M, pH 3) | Spike before hydrolysis: 60 Spike after hydrolysis: 65 | n.d. |
| BalanCD HEK | Spike before hydrolysis: 60 Spike after hydrolysis: 77 | n.d. |
| Freestyle 293 | Spike before hydrolysis: 85 Spike after hydrolysis: 84 | n.d. |
| Freestyle F17 | Spike before hydrolysis: 83 Spike after hydrolysis: 88 | n.d. |
| DMEM (Low Glucose 1 g/L) | Spike before hydrolysis: 64 Spike after hydrolysis: 72 | n.d. |
| DMEM (High Glucose 4.5 g/L) | Spike before hydrolysis: 55 Spike after hydrolysis: 59 | n.d. |
| OPTIMEM | Spike before hydrolysis: 50 Spike after hydrolysis: 74 | n.d. |
| D-PBS (+sucrose 1M) | Spike before hydrolysis: 43 Spike after hydrolysis: 78 | n.d. |
| BSS (NaCl 109.5 mM + KCl 10.1 mM + $CaCl_2$ 3.3 mM + $MgCl_2$ 1.4 mM + $C_2H_3NaO_2$ 28 mM + $Na_3C_6H_5O_7$ 5.8 pH 7.4 à 0.02% Tween) | Spike before hydrolysis: 62 Spike after hydrolysis: 73 | n.d. |
| D-PBS at 10% Glycerol | Spike before hydrolysis: 71 Spike after hydrolysis: 79 | n.d. |

TABLE 7-continued

| Examples of buffer with compound 17. | | |
|---|---|---|
| buffer | Recovery (%) | Degree of hydrolysis |
| Buffer 1: D-PBS at 6% Sorbitol at 0.05% Poloxamer 10% | Spike before hydrolysis: 87<br>Spike after hydrolysis: 94 | n.d. |
| Buffer 2: Glycine 50 mM + Tris 10 mM + NaCl 1000 mM + 2% Saccharose + 0.2% Pluronic in purified water | Spike before hydrolysis: 0<br>Spike after hydrolysis: 83 | n.d. |
| Buffer 3: 5% Tween 80 + HEPES 50 mM + NaCl 400 mM + MgCl2 20 mM + 1% Saccharose in Freestyle F17 | Spike before hydrolysis: 14<br>Spike after hydrolysis: 4 | n.d. |
| Buffer 4: 1% Tween 80 + HEPES 50 mM + NaCl 400 mM + MgCl2 20 mM + 1% saccharose in Freestyle F17 | Spike before hydrolysis: 21<br>Spike after hydrolysis: 10 | n.d. |
| Buffer 5: Tris 20 mM + NaCl 400 mM + 1% Saccharose + 5% Tween 80 in purified water | Spike before hydrolysis: 12<br>Spike after hydrolysis: 6 | n.d. |
| Buffer 6: HEPES 20 mM + MES 20 mM + Sodium Acetate 20 mM + NaCl 150 mM + CaCl2 5 mM in purified water | Spike before hydrolysis: 71<br>Spike after hydrolysis: 77 | n.d. |

The invention claimed is:

1. A method for performing an acidic hydrolysis of a liquid mixture comprising a biological matrix and a polyethyleneimine (PEI)-based transfection reagent, wherein the biological matrix comprises an adeno-associated virus (AAV) produced using the PEI-based transfection reagent, wherein the method comprises incubating the liquid mixture comprising the biological matrix in an aqueous solution comprising 0.1% (v/v) HCl at a temperature of 110° C. for 2 hours, wherein said acidic hydrolysis does not degrade the PEI-based transfection reagent, and wherein the PEI-based transfection reagent is of general formula (I) or an acceptable salt thereof:

(I)

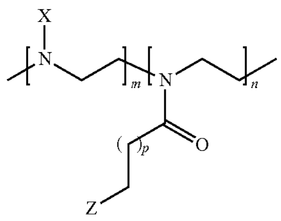

wherein:

m represents an integer between 198 to 300 and n represents an integer between 2 to 300, with the proviso that n is lower than m and the sum of min ranges from 200 to 600, X represents H, p represents an integer between 1 and 4, Z represents a group of formula:

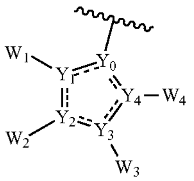

$Y_0$, $Y_1$, $Y_2$, $Y_3$ and $Y_4$, which may be identical or different, represent C or N, with the proviso that at least two, but no more than three, of $Y_0$, $Y_1$, $Y_2$, $Y_3$ and $Y_4$, are N, $W_1$, $W_2$, $W_3$ and $W_4$, which may be identical or different, represent H, methyl, cyclopropyl, isopropyl, tert-butyl, phenyl, benzyl, 2-pyridine, 3-pyridine, or 4-hydroxyphenethyl; or wherein (i) $W_1$ and $W_2$ or (ii) $W_2$ and $W_3$ or (iii) $W_3$ and $W_4$ together form a fused phenyl; a fused phenyl substituted by a methyl group, a methoxy group, a carboxyphenyl or Cl; a fused naphthalene; a fused 2-pyridine; or a fused 3-pyridine, with the proviso that at least one, but no more than two, of $W_1$, $W_2$, $W_3$ and $W_4$ is, or are, absent; and with the proviso that when $Y_1$ and $Y_2$ represent C and $Y_0$, $Y_3$ and $Y_4$ represent N, $W_1$ and $W_2$ do not form a fused 2-pyridine.

2. The method according to claim 1, wherein the PEI-based transfection reagent of general formula (I) has a grafting ratio defined as (n/(m+n))*100, and wherein the grafting ratio is ranging from 1 to 50%.

3. The method according to claim 1, wherein the PEI polymer backbone has weight average molecular weight (Mw) ranging from 1 kDa to 50 kDa.

4. The method according to claim 3, wherein the PEI polymer backbone has a weight average molecular weight (Mw) selected from the group consisting of 8, 10, 15, 22 and 30 kDa.

5. The method according to claim 1, wherein the PEI-based transfection reagent of general formula (I) is selected from the group consisting of the following compounds :

Compound 01
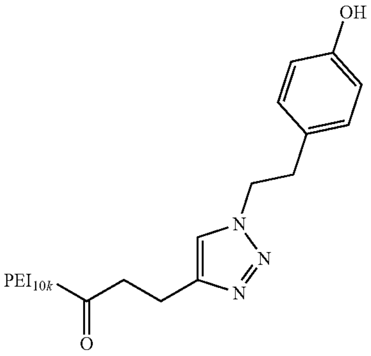
Compound 02
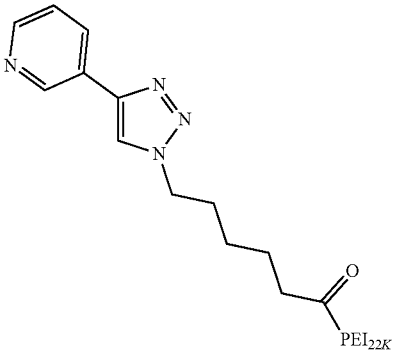
Compound 03
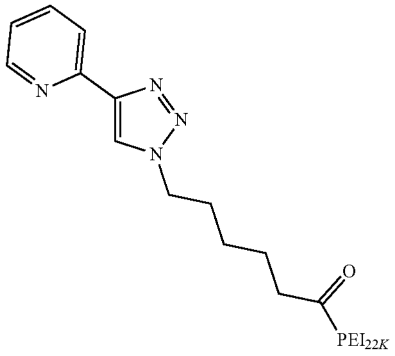
Compound 04
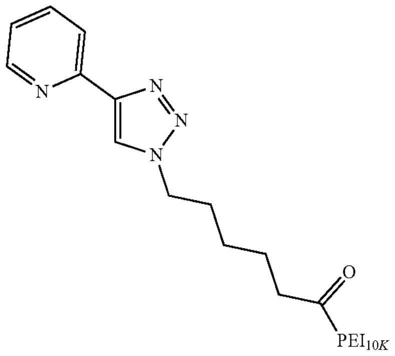
-continued
Compound 05
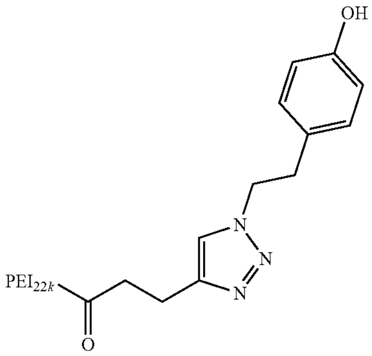
Compound 06
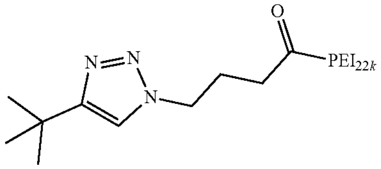
Compound 07
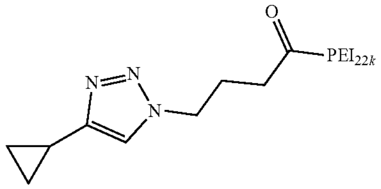
Compound 08
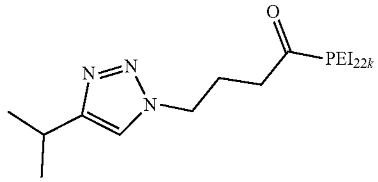
Compound 09
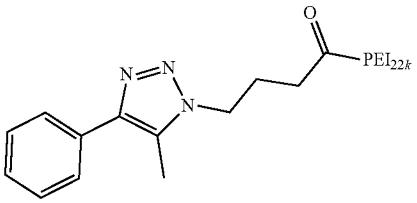
+
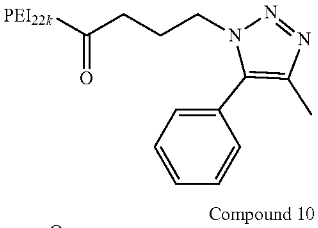
Compound 10
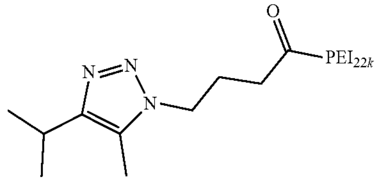

-continued
Compound 11
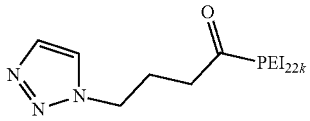
Compound 12
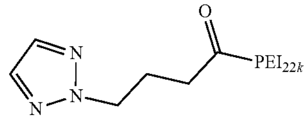
Compound 13
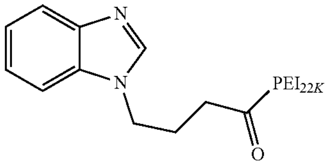
Compound 14
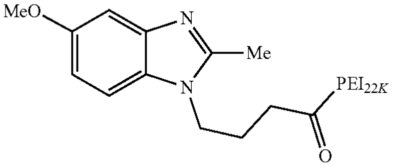
Compound 15
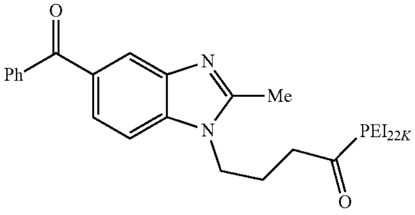
Compound 16
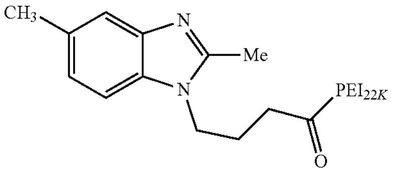
Compound 17
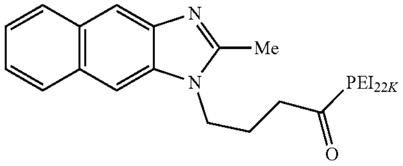
Compound 18
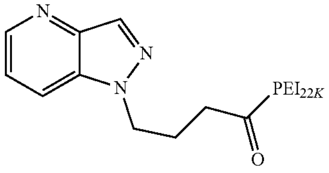
Compound 19
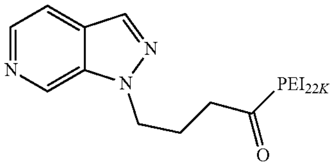
-continued
Compound 20
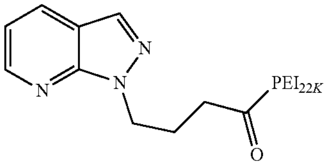
Compound 21
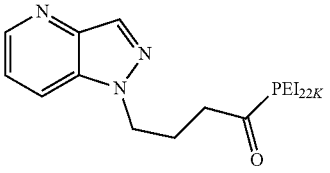
Compound 22
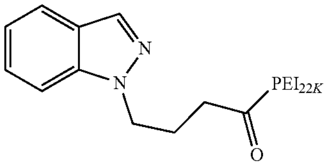
Compound 23
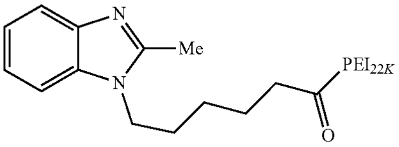
Compound 24
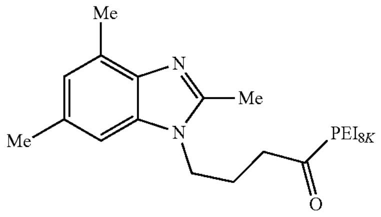
Compound 25
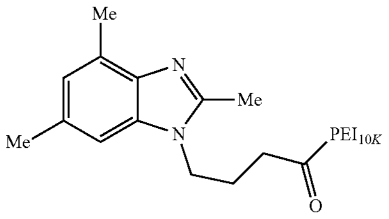
Compound 26
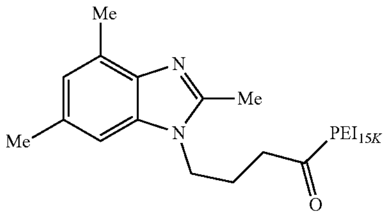
Compound 27
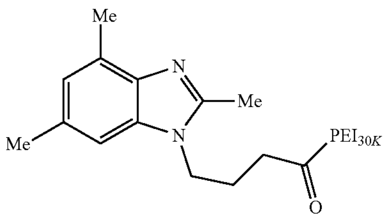

-continued

Compound 30

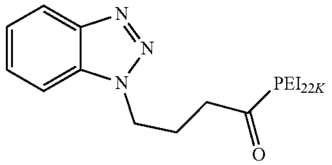

Compound 31

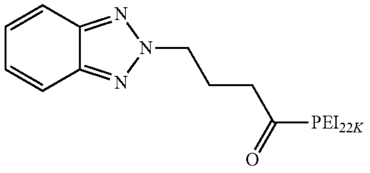

Compound 32

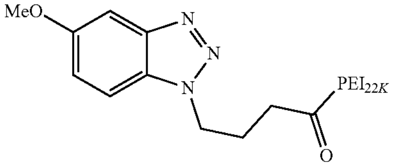

Compound 34

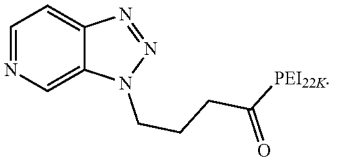

6. The method according to claim 5, wherein the PEI-based transfection reagent of general formula (I) is a compound selected from the group consisting of compounds 01, 02, 03, 04, 05, 06, 07, 08, 09, 10, 11, 12, 30, 31, 32 and 34.

7. The method according to claim 1, wherein the liquid mixture further comprises a component selected from the group consisting of a cell culture medium, a buffer, a solution used during manufacturing and purification of the AAV, and a composition comprising comprising pharmaceutically acceptable buffer and excipients used for the AAV in purified form.

8. A method for purifying, detecting and/or quantifying a polyethyleneimine (PEI)-based transfection reagent of general formula (I) as defined in claim 1, wherein the PEI-based transfection reagent of general formula (I) is comprised in a liquid mixture comprising a biological matrix, wherein the biological matrix comprises an adeno-associated virus (AAV) produced using the PEI-based transfection reagent of general formula (I) , wherein the method comprises :

(a) performing an acidic hydrolysis of the liquid mixture according to the method of claim 1, (b) purifying the reaction mixture obtained in step (a) in order to obtain a purified PEI-based transfection reagent of general formula (I), (c) detecting and/or quantifying the purified PEI-based transfection reagent of general formula (I) obtained in step (b).

9. The method according to claim 8, wherein step (c) is performed using High-performance liquid chromatography (HPLC) or Ultra high-performance liquid chromatography (UHPLC) analytical technique.

10. The method according to claim 8, wherein the PEI-based transfection reagent of general formula (I) of step (c) is detected with a limit of detection (LOD) ranging from 1 ppm to 1000 ppm, and/or a limit of quantification (LOQ) ranging from 1 ppm to 1000 ppm.

11. The method according to claim 1, wherein the PEI-based transfection reagent of general formula (I) is detectable in the liquid mixture during manufacturing of the AAV, and wherein the liquid mixture further comprises a component selected from the group consisting of a cell culture medium, a buffer, a solution used during manufacturing and purification of the AAV, and a composition comprising pharmaceutically acceptable buffer and excipients used for the AAV in purified form.

* * * * *